United States Patent
Fuks et al.

Patent Number: 5,968,758
Date of Patent: *Oct. 19, 1999

[54] METHOD FOR DETECTING FREE IGFBP-1

[75] Inventors: Boris Fuks, Mountain View, Calif.; Marina Boltovskaya, Moscow, Russian Federation; Alexander Konstantinov, Plainsboro, N.J.; Svetlana Nazimova; Nelli Starosvetskaya, both of Moscow, Russian Federation; Alexander Stepanov, Elektrostal, Russian Federation; Evgeny Zaraisky, Moscow, Russian Federation

[73] Assignee: California Research LLC, Mountain View, Calif.

[*] Notice: This patent is subject to a terminal disclaimer.

[21] Appl. No.: 08/740,104

[22] Filed: Oct. 28, 1996

Related U.S. Application Data

[63] Continuation-in-part of application No. 08/234,851, Apr. 28, 1994, Pat. No. 5,597,700.

[51] Int. Cl.⁶ .................................................. G01N 33/53
[52] U.S. Cl. ........................ 435/7.9; 435/7.1; 435/7.92; 435/7.94; 435/967; 435/969; 435/970; 436/514; 436/518; 436/25; 436/530; 436/810; 530/388.24
[58] Field of Search .................................. 435/7.92, 7.1, 435/7.94, 967, 969, 970, 7.9; 436/518, 530, 810, 525, 514; 530/388.24

[56] References Cited

U.S. PATENT DOCUMENTS

| | | |
|---|---|---|
| 4,235,601 | 11/1980 | Deutsch et al. . |
| 4,861,711 | 8/1989 | Friesen et al. ............................ 436/7.9 |
| 4,981,786 | 1/1991 | Dafforn et al. ............................ 435/7.9 |
| 5,006,474 | 4/1991 | Horstman et al. ........................ 436/524 |
| 5,120,643 | 6/1992 | Ching et al. ............................ 435/7.92 |
| 5,308,775 | 5/1994 | Donovan et al. ........................ 436/518 |

FOREIGN PATENT DOCUMENTS

| | | |
|---|---|---|
| 0 421 294 | 4/1991 | European Pat. Off. . |
| 2 204 398 | 11/1988 | United Kingdom . |
| 2 239 313 | 6/1991 | United Kingdom . |
| WO 92/12426 | 7/1992 | WIPO . |
| WO 94/00765 | 1/1994 | WIPO . |
| WO 94/17405 | 8/1994 | WIPO . |

OTHER PUBLICATIONS

Brewer et al., "Cloning, Characterization, and Expression of a Human Insulin–Like Growth Factor Bending Protein," Biochem Biophys Res. Comm. 152(3)1289–97, 1988.

Medix Biochemica Monoclonal Antibodies Catalog pp. 14–16, 18, 1988.

Wang et al, "Purification and Assay of Insulin–Like Growth Factor–Binding Protein–1 . . . " J of Endocrinol. 128:161–168, 1991.

Westwood et al. "The Phosphorylation Pattern of Insulin Like Growth Factor–Binding Protein–1 . . . " J. Clin. Endocr. Metabol. 79(6) 1735–41.

(List continued on next page.)

*Primary Examiner*—Carol A. Spiegel
*Attorney, Agent, or Firm*—William B. Walker

[57] ABSTRACT

Antibodies having binding affinity for free IGFBP-1, biological compositions including antibodies having binding affinity for free IGFBP-1, kits for detecting free IGFBP-1 using the antibodies, and cell lines for producing the antibodies are provided. Also provided are devices and methods for detecting free IGFBP-1 and a rupture in a fetal membrane based on the presence of amniotic fluid in a vaginal secretion, as indicated by the presence of free IGFBP-1 in the vaginal secretion. The antibodies that are provided may be characterized by their ability to selectively recognize those IGFBP-1 molecules which are free of IGF-1 and IGF-2, i.e., antibodies which have a binding affinity for free IGFBP-1 that is greater than a binding affinity of the antibody to bound IGFBP-1. These antibodies may also be characterized by their competition with IGF-1 and IGF-2 for binding to IGFBP-1.

6 Claims, 7 Drawing Sheets

OTHER PUBLICATIONS

Bell, S.C., et al., "Monoclonal Antibodies to Human Secretory 'Pregnancy–Associated Endometrial $\alpha_1$–Globulin,' An Insulin–Like Growth Factor Binding Protein: Characterization and Use in Raidoimmunoassay, Western Blots, and Immunohistochemistry", AJRI (American Journal of Reproductive Immunology) 20:3:87–96 (Jul. 1989).

Bell, S.C., et al., "N–terminal Amino Acid Sequence of Human Pregnancy–associated Endometrial $\alpha_1$–Gobulin, an Endometrial Insulin–like Growth Factor (IGF) Binding Protein—Evidence for Two Small Molecular Weight IGF Bindin Proteins, Endocrinology", (1988) vol. 123, pp. 1202 to 1204.

Bohn, H., et al., "Isolation and Characterization of a New Placenta Specific Protein ($PP_{12}$)", Arch. Gynecol 229, 279–291 (1980). In German & English Abstract.

Boltovskaya, et al., "Histochemical and Clinico–Diagnostiocal Study of the Placental Alpha–I–Microgobullin (PAMG–1) Using Monoclonal Antibodies", Bulletin of Experimental Biology and Medicine, USSR, Nr. 7, 1991, pp. 397–400. In Russian with English Abstract.

Friedman, M. L., et al., "Diagnosis of Ruptured Fetal Membranes", Am. J. Obst. & Gynec, Jun. 1969, pp. 544–550.

Hellemans, P., et al., "Preliminary Results with the Use of the ROM–check Immunoassay in the Early Detection of Rupture of the Amniotic Membranes", Eur. J. Ob. & Gyn and Repro. Biol. 43 (1992) 173–179.

Hodgkinson, S. C., et al., "Metabolic Clearance Rate of Insulin–like Growth Factor–I in Fed and Starved Sheep", J. Endroc. (1987) 115, 233–240.

Jones, John I., et al., "Insulin–Like Growth Factors and Their Binding Proteins: Biological Actions", Endocrine Reviews, 1995, pp. 3–34.

Keirse, M. J. N. C., et al., 43. "Prelabour Rupture of the Membranes Preterm, Effective Care in Pregnancy and Childbirth", Oxford U. Press, 1989, pp. 666–693.

Koistinen, R., et al., "Placental Protein 12 is a Decidual Protein that Binds Somatomedin and Has an Identical N–Terminal Amino Acid Sequence with Somatomedin–Binding Protein from Human Amniotic Fluid", Endocrinology, 118: 1375–1378 (1986).

Koninckx, P.R., et al., "Prolactin Concentration in Vaginal Fluid: A New Method for Diagnosing Ruptured Membranes", Brit. J. Ob. & Gyn., Jun. 1981, 88:607–610.

Lockwood, C.J., et al., "Fetal Fibronectin in Cervical and Vaginal Secretions as a Predictor of Preterm Delivery", N.E.J. Med, 1991 Sep. 5, pp. 669–674.

Lockwood, C.J., et al., "Fetal Membrane Rupture is Associated with the Presence of Insulin–like Growth Factor–Binding Protein–1 in Vaginal Secretions", Am J. Obstet. Gynecol., 171(1):146–150 (Jul. 1994).

Pekonen, F., et al., "A Monoclonal Antibody–based Immunoradiometric Assay for Low Molecular Weight Insulin–like Growth Factor Binding Protein/Placental Pretein 12.", J. Immunoassay, 10(4), 325–337 (1989).

Povoa, G., et al., "Cross–reaction of Serum Somatomedin–binding Protein in a Radioimmunoassay Developed for Somatomedin–binding Protein Isolated from Human Amniotic Fluid", Acta Endrocrinologica 1984, 107:563–570.

Rochelson, B.L., et al., "A Rapid Colorimetric AFP Monoclonal Antibody Test for the Diagnosis of Preterm Rupture of the Membranes", Ob. and Gyn. 69:163–165 (Feb. 1987).

Rochelson, B.L., et al., "Rapid Assay—Possible Application in the Diagnosis of Premature Rupture of the Membranes", Ob. and Gyn. 62:414–418 (Oct. 1983).

Roghani, M., et al., "Two Insulin–like Growth Factor (IGF)–Binding Proteins are Responsible for the Selective Affinity for IGF–II of Cerebrospinal Fluid Binding Proteins", J. Clin. Endro & Metabolism, 73–658–666 (1991).

Rutanen, E., et al., "Measurement of Insulin–like Growth Factor Binding Protein–1 in Cervical/Vaginal Secretions: Comparison with the ROM–check Membrane Immunoassay in the Diagnosis of Ruptured Fetal Membranes", Clinica Chimica Acta 214 (1993) 73–81.

Rutanen, E., et al., "Monoclonal antibodies to the 37–34K Insulin–like Growth Factor Binding Protein", Biochem. and Biophys. Res. Communications 152:1:208–215 (1988).

Smith, R. P., et al., "A Technic for the Delection of Rupture of the Membranes", Obstetrics and Gynecology, pp. 172–176, Aug. 1976.

Waites, G.T., et al., "Human 'Pregnancy–associated Endormetrial $\alpha_1$–globulin', an Insulin–like Growth Factor–binding Protein: Immunohistoloical Localization in the Decidua and Placenta During Pregnancy Employing Monoclonal Antibodies", J. Endorcinol. 120:351–357 (1989).

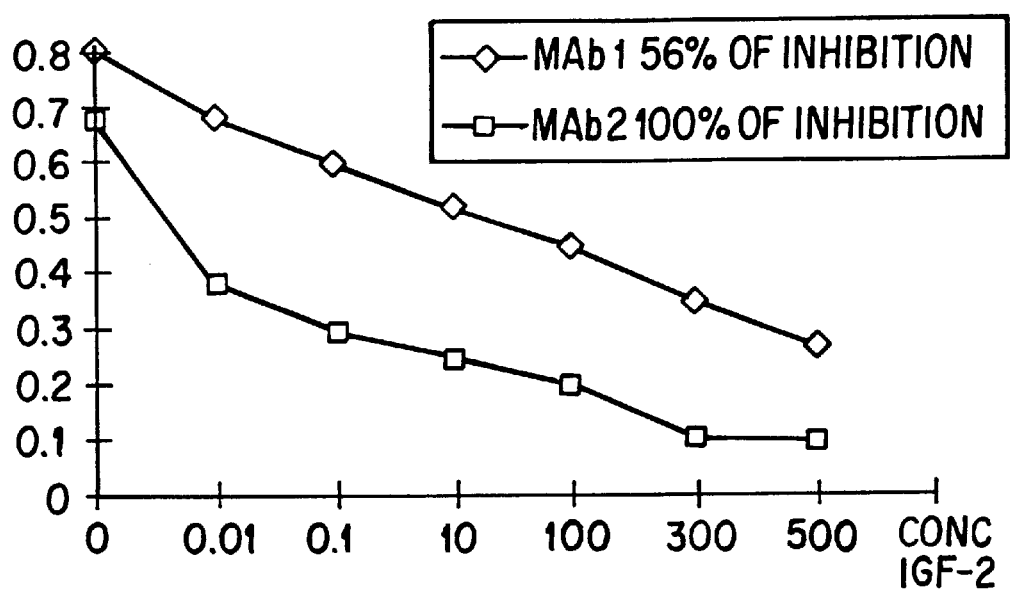
Fig_10
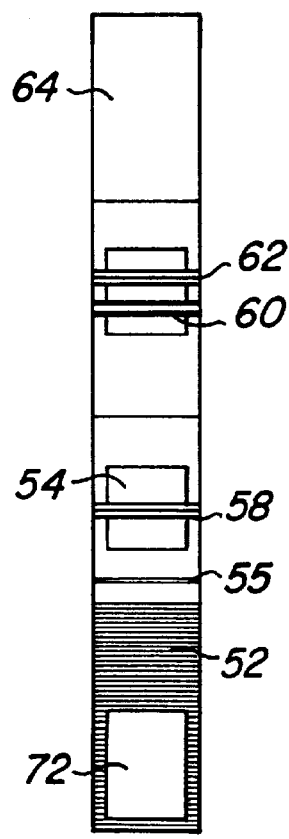
Fig_11

METHOD FOR DETECTING FREE IGFBP-1

CROSS REFERENCE

The present invention is a continuation-in-part of application Ser. No. 08/234,851, filed Apr. 28, 1994, entitled METHOD FOR DETECTING FREE INSULIN-LIKE GROWTH-FACTOR-BINDING PROTEIN 1 AND A TEST DEVICE FOR DETECTING THE RUPTURES OF FETAL MEMBRANES USING THE ABOVE METHOD, which issued as U.S. Pat. No. 5,597,700 on Jan. 28, 1997, is incorporated herein by reference in its entirety.

FIELD OF THE INVENTION

The present invention relates to antibodies, biological compositions, diagnostic methods and test devices for detecting a rupture in a fetal membrane based on the presence of amniotic fluid in a vaginal secretion. More specifically, the present invention relates to the detection of insulin-like growth-factor-binding protein 1 (IGFBP-1) cell line 1 (ATCC HB-12279) snf vrll linr 2 (ATCC 122780) from, uncomplexed to insulin-like growth-factor 1/(IGFBP-1) and insulin-like growth-factor 2 (IGF-2) (referred to here as free IGFBP-1) and its use in the detection of the presence of amniotic fluid in a vaginal secretion.

BACKGROUND OF THE INVENTION

Premature rupturing of fetal membranes (the membrane defining the amniotic sac) in pregnant women occurs in about 5% to 14% of all pregnancies and is the cause of about 10% of all perinatal deaths. When a fetal membrane rupture occurs toward the end of a pregnancy (38–40 weeks of pregnancy), delivery of the fetus should be effected as soon as possible in order to minimize the associated risks to the fetus and the mother. A simple, rapid and effective method for identifying fetal membrane ruptures is therefore needed so that the occurrence of a fetal membrane rupture toward the end of a pregnancy can be effectively monitored in order to limit the amount of time between the occurrence of the fetal membrane rupture and delivery.

Premature rupturing of fetal membranes is not a problem that is limited to the last few weeks of pregnancy. More than 30% of premature fetal membrane ruptures occur before 37 weeks of pregnancy. Fetal membrane ruptures before 37 weeks of pregnancy have been associated with significant increases in the risk of an intrauterine infection, Keirse M. J. N. C., et al., "Prelabor Rupture of the Membrane Preterm," in *Efficient Care in Pregnancy and Child-birth*, 1989, Vol. 1, Oxford, N.Y., Toronto. Edited by J. Chalmers, M. Enkin, and M. Keirse. Intrauterine penetration of such infections increase both maternal and perinatal mortality. The risk of intrauterine penetration of the intrauterine infection increases significantly as time passes between the rupture of the membrane and delivery. Early diagnosis of fetal membrane ruptures that occur before 37 weeks of pregnancy is therefore extremely important. Positive diagnosis of fetal membrane ruptures before 34 weeks of pregnancy is also important since it permits the timely monitoring and treatment of pregnant women to prevent intra-amnion infection and to stimulate fetal lung development.

A variety of methods have been developed for detecting fetal membrane ruptures. One method, called the crystallization test, detects amniotic fluid in vaginal secretions based on the observation of arborization, a tree-branch-like structure which forms when amniotic fluid dries on a slide. The crystallization test is described in M. L. Friedman and T. W. McElvin, *American Journal of Obstetrical Gynecology*, 1969, Vol. 104, pp. 544–550.

The crystallization test relies on the visual image produced on a slide by a vaginal secretion containing amniotic fluid being sufficiently visually distinct from normal vaginal secretions so as to enable the detection of amniotic fluid in a vaginal secretion. Because the crystallization test relies on the user to identify the presence of arborization in a test sample, the crystallization test is highly susceptible to user error. As a result, the accuracy of the crystallization test can be significantly operator dependent.

Many factors can cause a vaginal secretion sample to appear as though it contains amniotic fluid when it does not, and visa versa. For example, results obtained from the crystallization test can be erroneous if a long time has passed since the rupture has taken place. Vaginal infections can also influence the results of the crystallization test. It has been found that the crystallization test produces false results in as many as 20% of the cases, most commonly due to the pattern produced by a vaginal secretion being misidentified as containing amniotic fluid or not containing amniotic fluid.

A method has also been proposed for detecting fetal membrane ruptures based on the pH of a vaginal secretion where a detectable agent, such as a dye, is used to stain the amniotic fluid in vaginal secretion samples. M. L. Friedman and T. W. McElvin, *American Journal of Obstetrical Gynecology*, 1969, Vol. 104, pp. 544–550. Detection of fetal membrane ruptures based on the pH of vaginal secretions is inaccurate due to the susceptibility of the test to user error, as well as the variability of the pH of vaginal secretion samples person to person due to factors independent of the presence or absence of amniotic fluid in a vaginal secretion.

Methods have also been proposed for detecting fetal membrane ruptures based on an immunochemical analysis of the proteins contained in amniotic fluid. Immunochemistry is a branch of science that deals with the chemical changes and phenomena of immunity, specifically, the chemistry of antigens, antibodies, and their reactions. The proposed methods utilize the following four protein compounds for diagnosing fetal membrane ruptures: alpha-fetoprotrin, prolactin, fibronectin, and insulin-like growth-factor-binding protein 1 (IGFBP-1). B. L. Rochelson, et al., "Rapid Assay-Possible Application in the Diagnosis of Premature Rupture of the Membranes," in *Obstetr. Gynecol.*, 1983, Vol. 62, pp. 414–418; Koninckx, et al., "Prolactin Concentration in Vaginal Fluid: A New Method for Diagnosing Ruptured Membranes," *Br. J. Obstetr. Gynecol.* 1981, Vol. 88, pp. 607–610; P. Hellemans, et al., "Preliminary Results with the Use of Rom-Check Immunoassay in the Early Detection of Rupture of the Amniotic Membranes," *Eur. J. Obstetr. Gynecol. Reprod. Biol.*, 1992, Vol. 43, pp. 173–179; Rutanen, E. M., et al., "Measurement of Insulin-Like Growth-Factor Binding Protein-1 in Cervical/Vaginal Secretions: Comparison with the ROM-Check Membrane Immunoassay in the Diagnosis of Ruptured Fetal Membranes," *Clin. Chim. Acta*, 1993, Vol. 214, pp. 73–81).

Among the above immunochemical methods, those which are based on the detection of alpha-fetoprotein (AFP) and prolactin (PRL) in vaginal secretions are unreliable because the corresponding blood/amniotic fluid ratio of the above proteins varies considerably, i.e., between 1 and 10. In some cases, higher concentrations of proteins have been found in serum than in amniotic fluid. In addition, the concentration of amniotic proteins, such as alpha-fetoprotein, prolactin, and fibronectin, in amniotic fluid also varies during the course of a pregnancy. For example, AFP and PRL are present in amniotic fluid in high concentrations only during the second trimester (i.e., the second three-month period) of the pregnancy. As the pregnancy advances, the amniotic/serum protein concentration ratios for both these proteins decrease and is only about 3 to 4 at term.

Detection of fetal membrane ruptures based on the presence of fetal fibronectin in vaginal secretions has also been found to be unsatisfactory. P. Hellemans, et al., "Preliminary Results with the Use of the ROM-Check Immunoassay in the Early Detection of Rupture of the Amniotic Membranes," Eur. J. Obstetr. Gynecol. Reprod. Biol., 1992, Vol. 43, pp. 173–179; C. Lockwood, et al., "Fetal Fibronectin in Cervical and Vaginal Secretions as a Predictor of Preterm Delivery," in The New England Journal of Medicine, 1991, Vol. 325, pp. 669–674. The ROM-Check immunoassay taught by Hellemans, et al. is an immunochemical method based on the detection of fetal fibronectin.

Rutanen, et al. teaches an immunochemical method based on the detection of insulin-like growth-factor binding protein-1 (IGFBP-1). Rutanen, E.M., et al., "Measurement of Insulin-Like Growth-Factor Binding Protein-1 in Cervical/Vaginal Secretions: Comparison with the ROM-Check Membrane Immunoassay in the Diagnosis of Ruptured Fetal Membranes," Clin. Chim. Acta, 1993, Vol. 214, pp. 73–81). In this study, Rutanen, et al. teaches a ROM-Check membrane immunoassay with a false positive rate of 20% and a false negative rate of 9%.

The aforementioned methods for detecting fetal membrane ruptures based on the detection of alpha-fetoprotein, prolactin, fibronectin, and insulin-like growth-factor-binding protein 1 are not highly accurate, due, at least in part, to the many variable factors regarding the concentration of these proteins in amniotic fluid, and the relative concentration of these proteins in amniotic fluid to serum. The natural occurrence of these proteins in serum, albeit at a significantly lower concentration, creates a background noise level which can lead to the false identification of a fetal membrane rupture or the absence thereof. The background noise level due to the natural occurrence of these proteins in serum is particularly significant when the amount of amniotic fluid in the vaginal secretion sample is small. As a result, these methods are inaccurate and unreliable for the detection of fetal membrane ruptures.

At least one method has been developed for detecting fetal membranes ruptures based on the presence of IGFBP-1 in vaginal secretion samples at higher levels than is normally found in serum. International Patent Application WO 92/12426 to Eeva-Marja Rutanen, 1992. Two monoclonal antibodies (MAb 6303 and MAb 6305) which are capable of binding to IGFBP-1 are used in this method to determine the total amount of IGFBP-1 in a vaginal secretion sample. As will be discussed herein, antibodies MAb 6303 and MAb 6305 recognize functionally different antigenic determinants on the surface of the IGFBP-1 molecule than the antibodies of the present invention. It is the different antigenic determinants of the antibodies of the present invention which crucially determines their medical interest and their utility in the methods and devices of the present invention.

The method described in WO 92/12426 uses a method known as a two-site immunoradiometric assay which is described by F. Pekonen, et al., in Journal of Immunoassay, 1989, Vol. 10, pp. 325–337. More specifically, the method involves placing a vaginal secretion sample into a sample-holding plate containing one of the two monoclonal antibodies (MAb 6303 and MAb 6305). IGFBP-1 molecules contained in the vaginal secretion sample are attached to a first of the two antibodies which is present in the holding plate. A specially-labeled second antibody is then introduced and is connected to another site of the same IGFBP-1 molecule. Those labeled second antibodies which bind to the IGFBP-1 molecule are immobilized on the holding plate and are subsequently measured by methods known in the art, for example, by means of a radioactive counter.

Using the method described in WO 92/12426, one can quantitatively determine the amount of IGFBP-1 in a vaginal secretion sample. This method partially overcomes the disadvantages associated with the above described immunochemical methods by selecting a protein for analysis in which the blood/amniotic fluid ratio varies over the second and third trimesters within a narrower range than the immunochemical methods described above.

One serious drawback of the diagnostic method proposed by Rutanen et al. is that IGFBP-1 can be present in the blood in relatively large concentrations. For example, the concentration of all forms of IGFBP-1 in the blood sera of pregnant women ranges from 58 to 600 ng/mL (median 220 ng/mL). As a result, even small admixtures of serum can cause an increase in the level of IGFBP-1 detected in the sample to be significantly higher than the level of sensitivity (about 0.5 ng/mL) of the Rutanen method. For example, IGFBP-1 can be present in a vaginal secretion sample in a concentration range from 0.5 to 90 ng/mL in women with an intact fetal membrane. In addition, Rutanen assumes that even with the fetal membrane being intact, a trace amount of IGFBP-1 is still leaking into the vagina.

In order to reduce the frequency of false positive results in the Rutanen method based on the presence of a low concentration of IGFBP-1 in a vaginal secretion not due to a fetal membrane rupture, (for example, due to blood or IGFBP-1 leaking into the vagina from an intact membrane), the Rutanen method requires a relatively high concentration of IGFBP-1 to be detected (100 ng/mL) before being considered to indicate the presence of a fetal membrane rupture. For example, Rutanen treats the occurrence of a lower concentration of IGFBP-1 in a sample than the highest known concentration of IGFBP-1 in maternal serum as a determination that a fetal membrane rupture has not occurred. This approach, however, could cause the method described in WO 92/12426 to produce a high level of false negative results. For example, when the rupture is small or in its initial stage, the small increase in IGFBP-1 in the vaginal secretion relative to serum may not be sufficient to be recognized by the Rutanen method as a positive result. This severely limits the Rutanen method as a reliable early detection method.

All of the methods described above detect the presence of a fetal membrane rupture based on the detection of a biomolecule in a vaginal secretion which occurs in amniotic fluid at a higher level than in serum. A common disadvantage to all of these methods is the fact that the biomolecule being detected can also be present in appreciable amounts in serum. As a result, an unacceptably high level of false positive results can occur when the concentration of the biomolecule in the patient's serum is unusually high and an unacceptably high level of false negative results can occur when only a very small amount of amniotic fluid is present in the vaginal secretion.

A need therefore exists for a method for detecting fetal membrane ruptures based on the presence of a biomolecule in a vaginal secretion which occurs in amniotic fluid at a significantly higher level than in serum. The biomolecule should also occur in a lower concentration in serum than the biomolecules which have been previously used to detect fetal membrane ruptures.

A need also exists for a method which can detect fetal membrane ruptures based on the presence of amniotic fluid in a vaginal secretion with a high level of accuracy. In order to minimize the number of false negative results, it is important that the method be able to detect small concentrations of amniotic fluid in a vaginal secretion.

The above described methods are also designed generally for measuring the presence of a biomolecule in a relatively narrow range of its concentration. For example, some methods require dilution of the sample prior to testing. In order to broaden this range, multiple attempts to match the concentrations of the sample to the specific range of protein concentrations must be made. A need exists for a method which can be used over a wide range of biomolecule concentrations.

A further common disadvantage of the above-described methods is the significant amount of time required to perform these methods, as well as the amount of laboratory equipment and skill required to perform these methods. A need exists for a method which can be rapidly performed without appreciable laboratory equipment. A need also exists for a method whose accuracy is not operator dependent and can be performed by untrained personnel, such as the patient.

A variety of test devices which are based on visual color detection of various antigens are known. European Patent Application 421,294 A2 to E. Osikowic, 1991. However, a simple test kit suitable for rapidly detecting the presence of amniotic fluid in a vaginal secretion is not known. Although Rutanen specifies in WO 92/12426 that a special kit has been developed which may be used to carry out the method, no description of any test kit, except for the reagents used in the method for measuring the concentration of IGFBP-1 is provided. There are no drawings or any other physical description of the kit as a device. A need therefore exists for a test device and kit for detecting the presence of amniotic fluid in vaginal secretions.

SUMMARY OF THE INVENTION

The methods according to the present invention for detecting free IGFBP-1 include the use of one or more antibodies which are capable of selectively binding to those IGFBP-1 molecules which are free of IGF-1 and IGF-2. These antibodies may be characterized by their competition with IGF-1 and IGF-2 for binding to free IGFBP-1. These antibodies may also be characterized by their greater binding affinity for free IGFBP-1 than IGFBP-1 where IGF-1 and IGF-2 are bound thereto (bound IGFBP-1). These antibodies may be monoclonal or polyclonal antibodies, fragments thereof, or any molecule which has a binding affinity as specified in this application.

In one embodiment, the method for detecting free IGFBP-1 in a sample includes the step of contacting a sample containing free IGFBP-1 with an antibody which has a binding affinity for free IGFBP-1 according to the present invention such that the antibody forms an antibody-free IGFBP-1 complex, and the step of detecting the antibody-free IGFBP-1 complex, whereby the presence of the complex indicates the presence of free IGFBP-1 in the sample.

In another embodiment, the method for detecting free IGFBP-1 in a sample includes:

contacting a sample containing free IGFBP-1 with a first antibody which has a binding affinity for free IGFBP-1, the first antibody forming a first antibody-free IGFBP-1 complex;

contacting the sample with a second antibody having a binding affinity for free IGFBP-1, where at least one of the first and second antibodies possesses a binding affinity for free IGFBP-1 according to the present invention, the whereby second antibody binds to with the first antibody-free IGFBP-1 complex to form a first antibody-free IGFBP-1-second antibody complex; and detecting the first antibody-free IGFBP-1 -second antibody complex, the presence of which indicates the presence of free IGFBP-1 in the sample.

In another embodiment, the method for detecting free IGFBP-1 in a sample includes:

adding a sample to a first antibody region of material which permits migration of antibodies and proteins therethrough, the first antibody region including a first antibody which has a binding affinity for free IGFBP-1, introducing to the first antibody region a fluid sample containing free IGFBP-1, thereby resulting in the binding of the first antibody to free IGFBP-1 to form a first antibody-free IGFBP-1 complex;

allowing the sample to migrate to a test region of material, the test region containing a second antibody immobilized therein which has a binding affinity for free IGFBP-1, at least one of the first and second antibodies having a binding affinity for free IGFBP-1 that is greater than the antibody's binding affinity for bound IGFBP-1, whereby migration of the sample to the test region results in the second antibody binding to the first antibody-free IGFBP-1 complex to form an immobilized first antibody-free IGFBP-1-second antibody complex; and detecting the immobilized first antibody-free IGFBP-1-second antibody complex in the test region, the presence of which indicates the presence of free IGFBP-1 in the sample.

Variations of the above embodiment are provided which incorporate one or more control regions. In one variation, the method further includes the step of allowing the first antibody to migrate from the first antibody region to a where first control region, the first control region contains free IGFBP-1 bound thereto. Migration of the sample, along with the first antibody, to the first control region results in the first antibody forming a first antibody-free IGFBP-1 complex which is immobilized in the first control region. This is followed by the immobilized first antibody in the first control region, where the presence of the first antibody in the first control region indicates a low concentration of free IGFBP-1 in the sample.

In another variation, the method includes the step of allowing the first antibody-free IGFBP-1 complex from the first antibody region to migrate to a second control region. The second control region contains the second antibody bound thereto, and migration of the sample to the second control region results in the formation of a first antibody-free IGFBP-1-second antibody complex immobilized in the second control region, and further includes the step of detecting the immobilized first antibody in the second control region, where the presence of the first antibody in the second control region confirming the proper operation of the method.

BRIEF DESCRIPTION OF THE FIGURES

FIG. 3 is a schematic longitudinal sectional view of a device of the invention which may be used to detect the presence of free IGFBP-1 in order to diagnose the rupture of a fetal membrane.

FIG. 4 is a planar view of the device of FIG. 3, the internal structure of the device being seen through a thin transparent protective film.

FIG. 6 shows the labeled monoclonal antibody illustrated in FIG. 5 attached to its respective binding site of free IGFBP-1.

FIG. 10 is a plot showing the concentration of MAb-1 and MAb-2 versus the concentration of IGF-2 at which 56% inhibition of MAb-1 and 100% inhibition of MAb-2 binding to free IGFBP-1 occurs.

FIG. 11 illustrates a device having two control regions in which the test region and control regions are on the same fluid path.

DETAILED DESCRIPTION OF THE INVENTION

The present invention relates to antibodies having binding affinity for free IGFBP-1 (i.e., IGFBP-1 where IGF-1 and IGF-2 are not bound to the IGFBP-1 molecule) over bound IGFBP-1 (i.e., IGFBP-1 in which IGF-1 and IGF-2 is bound to the IGFBP-1 molecule), biological compositions including antibodies having binding affinity for free IGFBP-1, kits for detecting free IGFBP-1 using the antibodies of the present invention, and cell lines for producing antibodies of the present invention. The present invention also relates to devices and methods for detecting free IGFBP-1, as well as a fetal membrane rupture based on the presence of amniotic fluid in a vaginal secretion, as indicated by the presence of free IGFBP-1 in the vaginal secretion.

As will be described herein in greater detail, the present invention arises from the discovery that free IGFBP-1 occurs in amniotic fluid in significantly higher concentrations than in serum. The difference in the concentration of free IGFBP-1 in amniotic fluid and in serum enables one to detect the presence of amniotic fluid in a vaginal secretion based on the presence of free IGFBP-1 in the secretion. Further, because the presence of amniotic fluid in a vaginal secretion is indicative of a fetal membrane rupture, the detection of free IGFBP-1 in a vaginal secretion can also be used to detect a fetal membrane rupture.

As will also be described herein in greater detail, Applicants have developed antibodies which selectively bind to free IGFBP-1 over bound IGFBP-1. According to the present invention, these antibodies are incorporated into compositions of matter, kits, devices and methods useful for detecting free IGFBP-1 and the occurrence of a fetal membrane rupture based on the presence of free IGFBP-1 in a vaginal secretion.

As will also be described herein in greater detail, the methods and devices of the present invention may also be adapted to detect a biomolecule in a sample which has two distinct binding sites using two different antibodies which selectively bind to the two binding sites.

I. IGFBP-1, Bound IGFBP-1 and Free IGFBP-1

Figure 1:
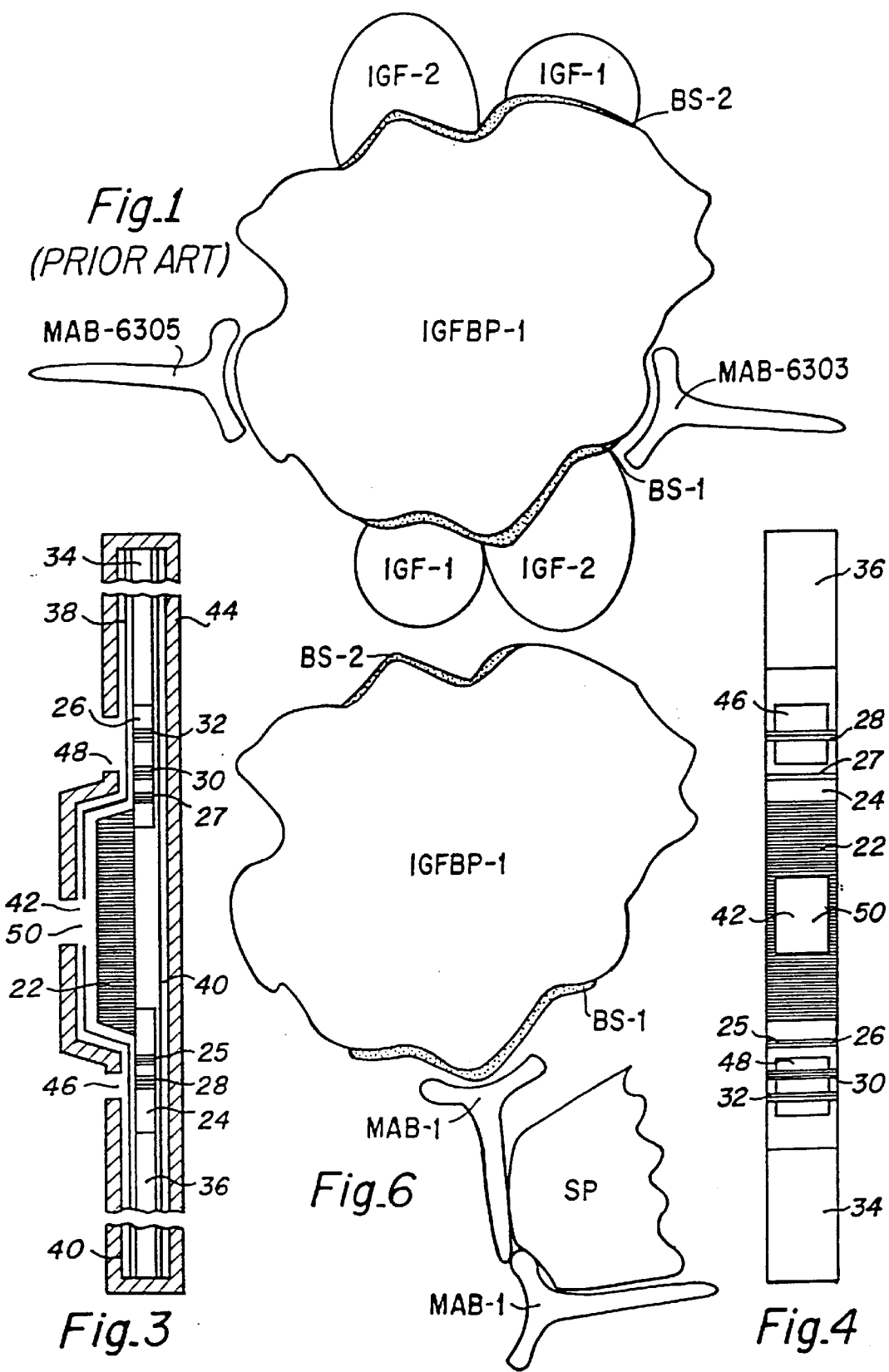
FIG. 1 is a schematic diagram illustrating IGFBP-1 with IGF-1 and IGF-2 attached to specific binding sites BS-1 and BS-2 as well as the interaction of antibodies with IGFBP-1, non-competitive with IGF-1 and IGF-2 [prior art].

Insulin-like growth-factor-binding protein 1 (IGFBP-1) is a protein which is present in the sera and amniotic fluid of pregnant women. As illustrated in FIG. 1, IGFBP-1 has two binding sites, BS-1 and BS-2, for the connection of two growth factors, i.e., insulin-like growth factor 1 (IGF-1) and insulin-like growth factor 2 (IGF-2). IGF-1 and IGF-2 are proteins which regulate the metabolism of carbohydrates in a human body and are usually present in the blood. Although IGFBP-1 itself does not directly control carbohydrate metabolism, it functions as a carrier for IGF-1 and IGF-2.

Figure 2:
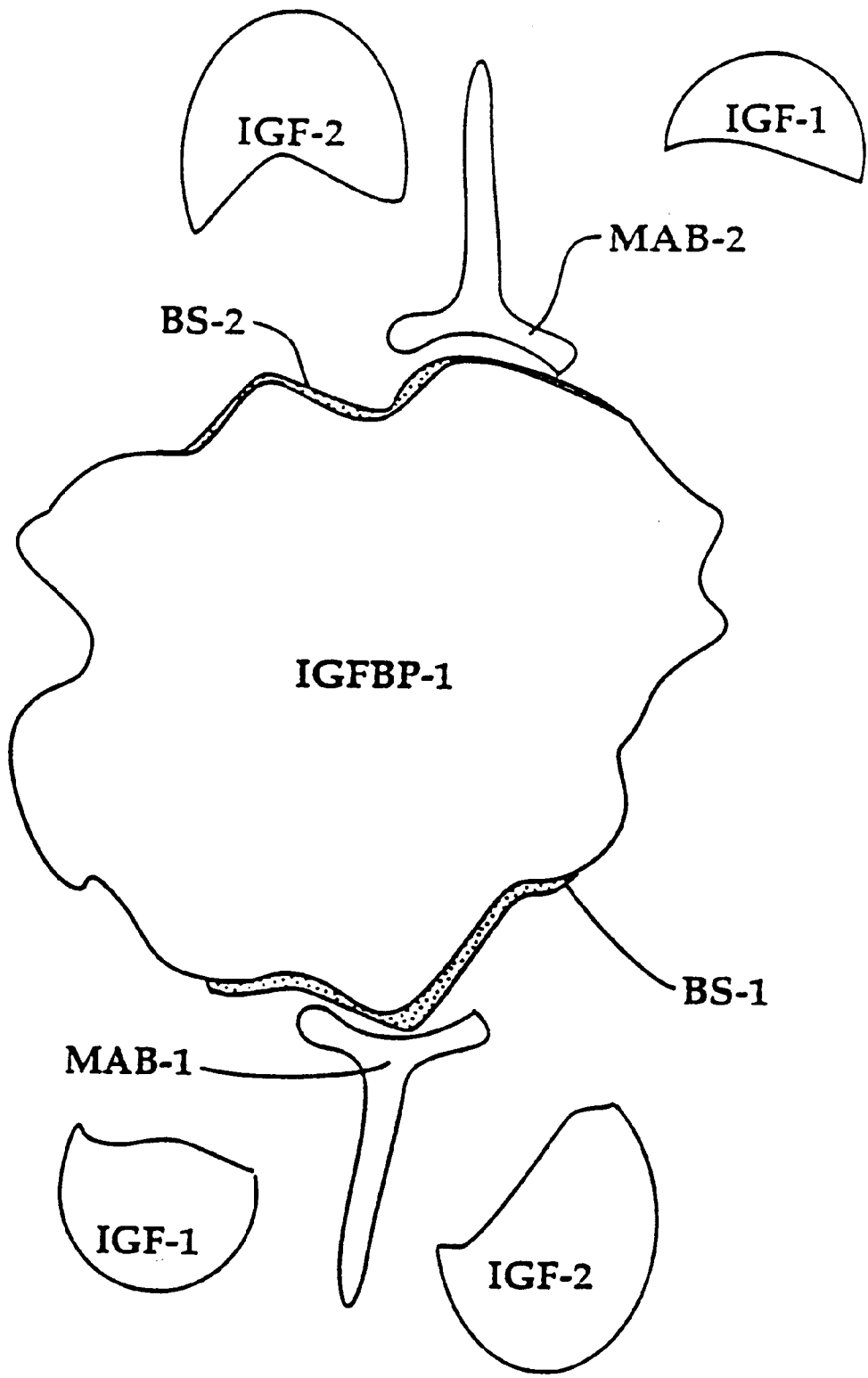
FIG. 2 is a schematic diagram illustrating MAb-1 and MAb-2 binding to binding sites BS-1 and BS-2 of IGFBP-1 and competitively inhibiting binding of IGF-1 and IGF-2 to IGFBP-1.

IGFBP-1 occurs in the body where insulin-like growth-factor 1 (IGF-1) and insulin-like growth-factor 2 (IGF-2) are bound to IGFBP-1 (bound IGFBP-1), as illustrated in FIG. 1, and where IGF-1 and IGF-2 are not bound to IGFBP-1 (free IGFBP-1), as illustrated in FIG. 2. As used herein, IGFBP-1 refers to the protein itself, regardless of whether one or more growth factors are bound to it.

IGFBP-1 occurs in both the serum and amniotic fluid of pregnant women and is present in amniotic fluid in a significantly higher concentration than in serum (22K–350K ng/mL amniotic fluid; 58–600 ng/mL serum). WO 94/00765. Of the IGFBP-1 present in the serum and amniotic fluid of pregnant women, IGFBP-1 is mostly present in the form of bound IGFBP-1. By contrast, Applicants have discovered that free IGFBP-1 occurs in the amniotic fluid of pregnant women in concentrations between about 1000–250,000 ng/mL (26,000 ng/mL average) and occurs in significantly lower concentrations in serum (3–47 ng/mL; 21 ng/mL average). See Tables 3 and 4.

IGFBP-1 was at first isolated in 1977 from the placenta by D. Petrunin and was originally referred to as placenta-specific alpha-macroglobulin 1 (PAMG-1). D. Petrunin, et al., "Immunological Identification of Alpha-1 Macroglobulin of Placenta and Its Content in the Amniotic Fluid," in *Akusherstvo i Ginekologiya*, 1977, N 1, 64–65, Moscow.

An analogous protein, identified as PP12, (placental protein 12) was later purified from placenta and fetal membranes by Bohn, et al., "Isolierung und Characterisierung eines Neuen Placentaspezifischen Proteins (PP12)," in *Arch. Gynecol.*, 980, Vol. 229, pp. 279–291.

It was later observed that PP12 and IGFBP-1 have the same N-terminal amino acid sequence (Povoa, et al., "Cross-Reactions of Serum Somatomedin-Binding Protein in a Radioimmunoassay Developed for Somatomedin-Binding Protein Isolated from Human Amniotic Fluid," *Acta Endocrinologica*, 1984, Vol. 107, pp. 563–570). It was also observed that PP12 binds to IGF-1 (Koistinen, et al., "Placental Protein 12 is a Decidual Protein that Binds Somatomedin and Has an Identical N-Terminal Amino Acid Sequence with Somatomedin-Binding Protein from Human Amniotic Fluid," in *Endocrinology*, 1986, Vol. 118, p. 1375).

S. Bell, et al. reported the separation of endometrial alpha$_1$-globulin (PEG-1), a protein having an immunochemical identity with PP12 but differing from PP12 by two amino acid substituents (amino acids N11, 12) in the N-terminal peptides of 15 amino acids. S. Bell, et al., *Amer. J. Reproductive Immunology*, 1989 Vol. 20, p. 87–96. IGFBP-1, PP12 and alpha$_1$-PEG were found to have no distinctions in their physiochemical and immunological properties.

In order to further characterize the proteins identified from amniotic fluid, Applicants conducted a series of measurements for determining the molecular weight of IGFBP-1. Using an immunoblotting method, Applicants determined the molecular weight of IGFBP-1 was 32 kD (kD is an atomic mass unit) (M. N. Boltovskaya et al., "Histochemical and Clinico-Diagnostic Study of the Placental A-Macroglobulin [PAMG-1] Using Monoclonal Antibodies," in Bull Exp. Biol. Med., 1991, No. 10, pp. 397–400).

The protein studied by Rutanen et al. was reported to have a molecular weight equal to about 35 kD (Rutanen et al., Clinica Chimica Acta, 1993, pp 73–81). Prior to this paper, Rutanen had reported a broader weight range, i.e., 25 to 34 kD (International Patent Application WO 92/12426).

Based on the fact that the amniotic proteins described above (IGFBP-1, PP12, alpha$_1$-PEG) have different molecular weights while having similar structural and functional properties, Applicants assumed that there is a family of proteins which include the proteins mentioned above.

II. Antibodies To IGFBP-1 and Free IGFBP-1

As FIG. 1 illustrates, IGFBP-1 has two binding sites, BS-1 and BS-2, for IGF-1 and IGF-2. The presence of the above two sites was discovered by M. Roghani who showed that two insulin-like growth factor (IGF)-binding proteins are responsible for the selective affinity of IGF-2 for cerebrospinal fluid-binding proteins. Roghani, et al., in J. Clinical Endocr. Metabol., 1991, Vol. 73, pp. 658–666.

The linkage of IGFBP-1 with IGF-1 and IGF-2 is evidently very strong and stable. S. C. Hodkinson and colleagues have demonstrated that, after administration, IGF-1 and IGF-2 were bound to IGFBP-1 with high affinity in minutes, S. C. Hodkinson et al., "Metabolic Clearance Rate of Insulin-Like Growth-Factor 1 in Fed and Starved Sheep," in J. Endocrinol., 1987, Vol. 115, pp. 233–240.

WO 92/12426 reports two monoclonal antibodies (MAb 6303 and MAb 6305) which are capable of binding to IGFBP-1 and which are used in a method to determine the total amount of IGFBP-1 in a vaginal secretion sample. These antibodies do not compete with IGF-1 and IGF-2 for binding to IGFBP-1. As illustrated in FIG. 1, the binding sites for these antibodies do not appear to overlap with the binding sites for IGF-1 and IGF-2.

By contrast to the monoclonal antibodies reported in WO 92/12426, Applicants have developed antibodies which are capable of recognizing only those IGFBP-1 molecules which are free of IGF-1 and IGF-2. These antibodies have been characterized by their competition with IGF-1 and IGF-2 for binding to free IGFBP-1 and their selectivity for free IGFBP-1. A process for producing hybridomas against IGFBP-1 and for selecting antibodies having a binding affinity according to the present invention is described in the examples to this application. From the tables presented in the examples and FIG. 10, one can see that the quantity of antibodies bound to free IGFBP-1 gradually decreases as the concentration of IGF-1 and IGF-2 increases. The level of inhibition sometimes reaches 100%. Consequently, the binding affinity to free IGFBP-1 is significantly greater than the binding affinity of the antibodies bound to bound IGFBP-1.

Two monoclonal antibodies having a binding affinity according to the present invention are designated MAb-1 and MAb-2. These antibodies are produced by hybridoma cell lines 1 and 2, respectively. Cell lines producing the monoclonal antibodies referred to herein as MAb-1 and MAb-2 were accepted for deposit on Jan. 31, 1997 by the American Type Culture Collection (ATCC), an International Depository Authority, 10801 University Boulevard Manassas, Va. 20110-2209 and assigned the ATCC accession numbers HB-12279 and HB-12280, respectively.

Applicants have demonstrated that growth factors IGF-1 and IGF-2 strongly compete with the antibodies of the present invention against those IGFBP-1 molecules (PAMG-1 as identified by D. Petrunin, et al.) which do not include IGF-1 and IGF-2, i.e. free IGFBP-1. This observation confirms that PAMG-1, as identified by D. Petrunin, et al., is functionally identical to IGFBP-1.

MAb-1 and MAb-2 have been found not to compete with one another with respect to free IGFBP-1. This is strong evidence that the binding sites of IGFBP-1 for both antibodies have different structures and thus have a different location on the surface of the IGFBP-1 molecule. Roghani, et al. assumes that the N-terminal domain common to IGFBP-1, IGFBP-2 and IGFBP-3 contains binding sites for both IGF-1 and IGF-2, but that the high-affinity binding site for IGF-2 is in fact located in some other region.

Without being bound by theory, Applicants believe that IGFBP-1 has two separate IGF-binding sites. One main theory behind the present invention is that antibodies such as MAb-1 and MAb-2 both compete with IGF-1 and IGF-2 for their binding sites located on the IGFBP-1 molecule.

III. Antibodies According to the Present Invention

The present invention relates to antibodies which are capable of selectively recognizing those IGFBP-1 molecules in a sample which are free of IGF-1 and IGF-2. These antibodies may be characterized by their competition with IGF-1 and IGF-2 for binding to IGFBP-1. As a result of their competition with IGF-1 and IGF-2, the antibodies of the present invention exhibit a greater binding affinity for free IGFBP-1 than bound IGFBP-1. This greater binding affinity is used in the present invention to identify free IGFBP-1 in a sample which also contains bound IGFBP-1 based on the formation of an antibody-free IGFBP-1 complex.

As used herein, the term "antibody" refers to any protein having a binding affinity as specified in this application, independent of the manner by which the protein is formed. For example, the protein may be a monoclonal or polyclonal antibody or fragment thereof, or any molecule having a binding specificity as specified in this application.

Antibodies according to the present invention may produced by standard monoclonal or polyclonal antibody production techniques and are preferably produced by raising the antibody against free IGFBP-1. It is noted that the antibodies may be raised against a mixture of bound and free IGFBP-1 (e.g., the mixture of IGFBP-1 found in amniotic fluid) and is preferably raised against purified free IGFBP-1.

In a preferred embodiment, the antibody is a monoclonal antibody. Two examples of monoclonal antibodies according to the present invention are MAb-1 and MAb-2 which are produced by cell line 1 (ATCC HB-12279) and cell line 2 (ATCC 122780) respectively. Antibodies according to the present invention also include those antibodies which compete with a monoclonal antibodies produced by ATCC designation HB-12280 for binding to free IGFBP-1.

In one embodiment, monoclonal antibodies according to the present invention are produced by the following process. First, a mammal having spleen and lymph node B-cells is immunized with IGFBP-1. Hybridomas are then produced to immortalize the B-cells. The B-cells may be spleen and/or lymph node B-cells. Those hybridomas which produce a monoclonal antibody having a binding affinity for IGFBP-1 are then identified. Of the hybridomas identified, those hybridomas which produce antibodies which compete with IGF-1 and IGF-2 for binding to IGFBP-1 are identified. These identified hybridomas are then cultivated in vitro or in ascites and the monoclonal antibodies they produce are isolated.

IV. Compositions According to the Present Invention

The present invention is also directed to a series of compositions which include one or more antibodies according to the present invention. In one embodiment, the composition includes an antibody and a detectable marker attached to the antibody. A variety of detectable markers may be used including, but not limited to, stained particles, enzymes, dyes and radioactive isotopes. One particular example of a detectable marker is a gold stained particle having an average dimension within the range of 20 to 40 nm. Another example of a detectable marker is a fluorescent dye. For example, methods for attaching a detectable marker to an antibody are described in *Methods In Enzymology,* 1981, Vol. 73, pp. 3–46; Harlow, E., and Lane, D., in *ANTIBODIES A LABORATORY MANUAL,* Cold Spring Harbor Laboratory, 1988, pp. 322, 323, and 343; and Pierce Catalog, pp. T-9–T-17 (1996).

In another embodiment, the composition includes an antibody having a binding affinity according to the present invention and free IGFBP-1. In this embodiment, the composition may further include a detectable marker attached to the antibody. The composition may also include a second antibody bound to free IGFBP-1. In this regard, the second antibody should be immunologically distinct from the first antibody so that the first and second antibodies can simultaneously bind to free IGFBP-1. It is envisioned that the second antibody may be any antibody that is capable of binding to free IGFBP-1 and need not necessarily be an antibody which competes with IGF-1 and IGF-2 for binding to free IGFBP-1, i.e., the antibody may bind to other binding sites on the IGFBP-1 molecule than BS-1 and BS-2. However, the second antibody is preferably an antibody which has a binding affinity according to the present invention.

V. Kits According to the Present Invention

The present invention also relates to kits for detecting free IGFBP-1. In one embodiment, the kit includes a first antibody according to the present invention and a second antibody which has a binding affinity for IGFBP-1. The second antibody should be immunologically distinct from the first antibody such that the first and second antibodies can simultaneously bind to free IGFBP-1. It is envisioned that the second antibody may be any antibody that is capable of binding to free IGFBP-1 and need not necessarily be an antibody which competes with IGF-1 and IGF-2 for binding to free IGFBP-1, i.e., the antibody may bind to other binding sites on the IGFBP-1 molecule than BS-1 and BS-2. However, the second antibody is preferably an antibody which has a binding affinity according to the present invention.

In one variation of the kit, the first or second antibody includes a detectable marker attached to the antibody. In another variation, the first or second antibody is attached to a solid support. In a preferred variation, the first or second antibody includes a detectable marker and the antibody which does not include a detectable marker is attached to a solid support.

VI. Cell Lines According to the Present Invention

The present invention also relates to cell lines which produce antibodies according to the present invention. Two examples of such cell lines are cell line 1 (ATCC HB-12279) and cell line 2 (ATCC designation HB-12280. Also included are cell lines which produce monoclonal antibodies which compete with monoclonal antibodies produced by cell line 1 (ATCC HB-12279) or cell line 2 (ATCC 122780).

In one embodiment, a cell line according to the present invention is produced by the following process. First, a mammal having spleen B-cells and lymph node cells is immunized with IGFBP-1. Hybridomas are then produced to immortalize the B-cells. The B-cells may be spleen and/or lymph node B-cells. Those hybridomas which produce a monoclonal antibody having binding affinity for IGFBP-1 are then identified. Of the hybridomas identified, those hybridomas which produce antibodies which have a binding affinity according to the present invention are identified. Selection of the antibodies may be, for example, based on their competition with IGF-1 and IGF-2 for binding to IGFBP-1. The hybridomas identified by this process are included among the cell lines of the present invention.

VII. Devices & Methods for Detecting Free IGFBP-1

The present invention also relates to devices and methods for detecting free IGFBP-1 in a sample. The present invention also relates to the use of these devices and methods for detecting the occurrence of a fetal membrane rupture based on the detected presence of free IGFBP-1 in a vaginal secretion.

Free IGFBP-1 occurs in amniotic fluid at a concentration about 1000 times greater than in serum. Free IGFBP-1 also occurs in serum at a concentration about 10 times less than the concentration of all forms of IGFBP-1. As a result, even when a small amount of amniotic liquid is contained in a vaginal secretion sample, a sufficient amount of free IGFBP-1 is present in the vaginal secretion sample to evidence that a fetal membrane rupture has taken place. Further, because of the low concentration of free IGFBP-1 in blood serum, the non-significant admixture of serum to the sample does not affect the results produced by the devices and methods of the present invention.

It is noted that Applicants were the first to identify that free IGFBP-1 occurs in amniotic fluid in significantly higher concentrations than in serum. It is the realization of this significant difference in the concentration of free IGFBP-1 in amniotic fluid and in serum which enables one to detect the presence of amniotic fluid in a vaginal secretion based on the presence of free IGFBP-1 in the secretion. Because the presence of amniotic fluid in a vaginal secretion is indicative of a fetal membrane rupture, the detection of free IGFBP-1 in a vaginal secretion can also be used to detect a fetal membrane rupture.

The devices and methods according to the present invention for detecting free IGFBP-1 and fetal membrane ruptures are highly sensitive and accurate. For example, concentrations of 5 ng/mL free IGFBP-1 and lower can be detected according to the present invention. Because the average concentration of free IGFBP-1 in serum is only about 21 ng/mL, as compared to an average concentration of about 25,000 ng/mL in amniotic fluid, a lower detection limit for free IGFBP-1 can be used in the method of the present invention for detecting the occurrence of a fetal membrane rupture. By using a lower detection limit, most false negative results are avoided. In addition, fetal membrane ruptures can be detected at an earlier stage since the devices and methods do not practically depend on the amount of the amniotic fluid which has seeped into the sample.

The devices and methods are designed to avoid producing false positive results through the use of antibodies which are highly specific for free IGFBP-1. As a result, the devices and methods are not influenced by the presence of vaginal infections or other variables which have reduced the accuracy of prior methods for detecting fetal membrane ruptures. In addition, the large ratio between serum and amniotic free IGFBP-1 makes the methods and devices significantly less likely to produce false positive results due to the presence of serum in vaginal secretions, even when a low free IGFBP-1 detection limit is used. For example, Applicants did not detect an increase in free IGFBP-1 in the absence of a fetal membrane rupture which might be attributed to decidual cell leakage. Further, the test is not limited from the standpoint of age of gestation of the fetus because the concentration of free IGFBP-1 in amniotic fluid does not vary significantly over the term of the pregnancy.

As described herein, the devices and methods can be adapted to be easily used in a rapid and convenient manner, thereby making it possible for the devices and methods to be used under outpatient conditions. For example, the method can be incorporated into an easy-to-use device which can be operated by a patient with little or no prior experience with the device. No special timing, dilution or matching of the sample concentrations prior to measurement is required in order to perform the method or use the device. For example, the device may be designed to be equally suitable for low and high concentrations of free IGFBP-1 in the vaginal secretion sample. This makes the method highly reliable and not highly susceptible to operator error. The method can also be designed to enable a simple yes/no determination of the presence of free IGFBP-1 in a sample and the presence of a fetal membrane rupture. The methods and devices are also designed to be simple and inexpensive and do not require any expensive instrumentation to utilize.

A. Devices for Detecting Free IGFBP-1

A variety of devices are envisioned for detecting free IGFBP-1. A preferred embodiment of a device according to the present invention for detecting free IGFBP-1 in a sample is described in example 9 and in FIGS. 3–9. Devices according to the present invention preferably can detect free IGFBP-1 in a sample where the concentration of free IGFBP-1 in the sample is between about 5 ng/mL and 250 $\mu$g/mL. It is also preferred that the devices have detection limits of at least about 5 ng/mL.

In this section, different possible embodiments of devices according to the present invention, embodied within the device illustrated in FIGS. 3–9, will be described. It is noted that these devices can be designed to simply detect the presence of free IGFBP-1, as in the devices described in Section A(1). These devices can also include one or more control regions for confirming the proper operation of the device. Examples of devices with one or more control regions are described in Section A(2). It should be noted, however, that alternative control region designs may also be used with the devices of the present invention.

Although the devices described in this section provide a qualitative determination of the presence of free IGFBP-1, it should be noted that these devices can be readily adapted for quantitatively determining the concentration of free IGFBP-1 in a sample, for example by detecting free IGFBP-1 using a detectable marker and using a calibration curve to calibrate the amount of free IGFBP-1 detected.

1. Devices without Control Regions

In one embodiment, the device includes a first antibody region 22 formed of a material which permits migration of antibodies and proteins therethrough. The first antibody region 22 also includes a first antibody which is capable of binding to free IGFBP-1. Introduction to the first antibody region 22 of a fluid sample containing free IGFBP-1 results in the attachment of the first antibody to free IGFBP-1 to form a first antibody-free IGFBP-1 complex as illustrated in FIG. 6.

Figure 7:
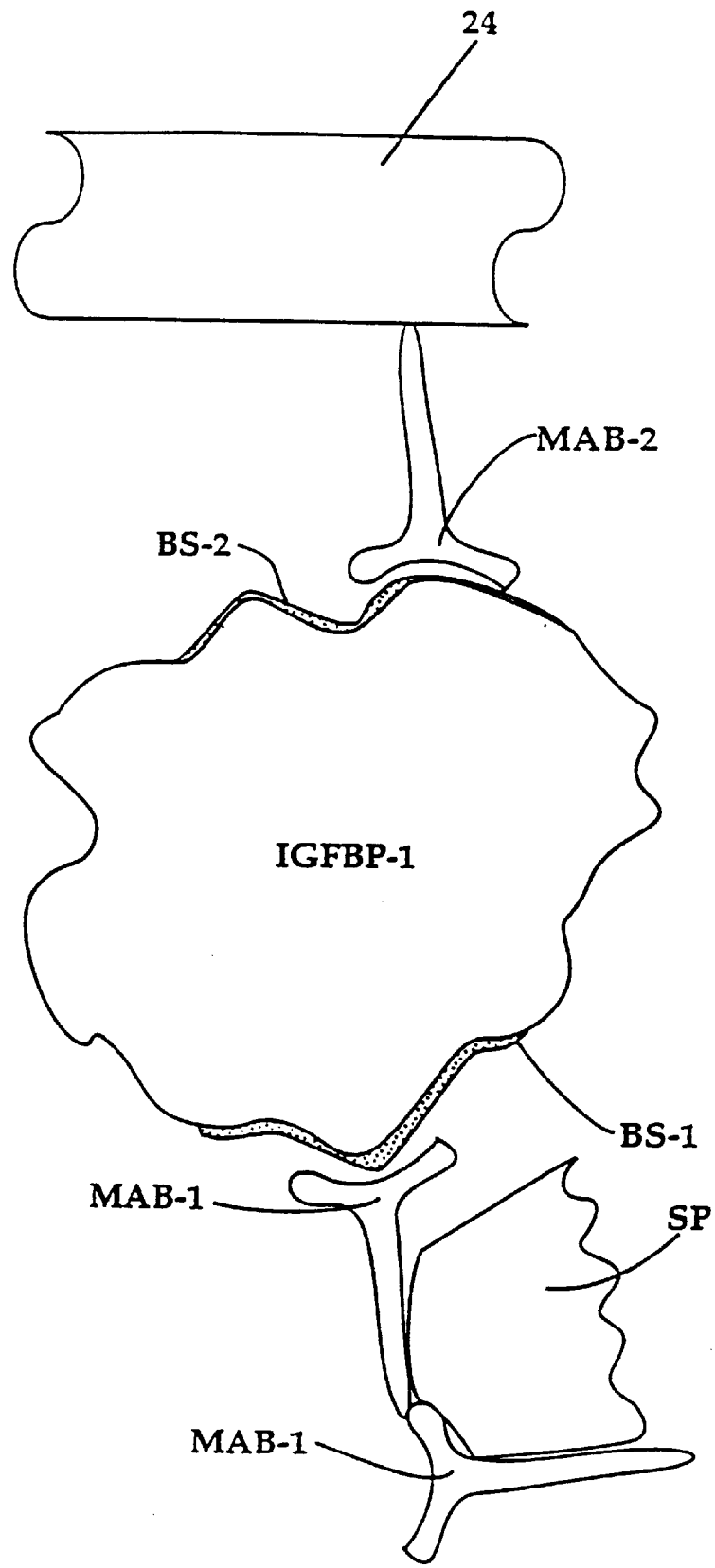
FIG. 7 shows a complex of FIG. 6 which is attached to a second monoclonal antibody which is stationary, bound to a solid phase such as the material of a nitrocellulose strip in the test region of the device of FIG. 3.

The device also includes a test region 28 in fluid connection with the first antibody region 22 formed of a material which permits migration of antibodies and proteins therethrough. The test region 28 includes a second antibody immobilized in the test region 28 which is also capable of binding to free IGFBP-1. The second antibody is immunologically distinct from the first antibody such that the first and second antibodies can simultaneously bind to free IGFBP-1. Introduction of a fluid sample to the first antibody region 22 results in the migration of the first antibody-free IGFBP-1 complex, illustrated in FIG. 6, into the test region 28 where the first antibody-free IGFBP-1 complex binds to the second antibody and is immobilized in the test region by the second antibody, as illustrated in FIG. 7. The device detects free IGFBP-1 in a sample based on the presence of the first antibody immobilized in the test region 28.

According to this embodiment, at least one of the first and second antibodies is an antibody according to the present invention. As a result, only free-IGFBP-1 forms a first antibody-free IGFBP-1-second antibody complex which is immobilized in the test region 28. As a result, the presence of the first antibody immobilized in the test region 28 is indicative of the presence of free IGFBP-1 in the sample. In one embodiment, the first antibody is an antibody according to the present invention and in another embodiment, the second antibody is an antibody according to the present invention. In a preferred embodiment, both the first and second antibodies are antibodies according to the present invention.

In a variation of the device, the first antibody includes a detectable marker which is used to detect free IGFBP-1 immobilized in the test region 28 by the marker's presence in the test region 28. Examples of detectable markers which may be used include, but are not limited to stained particles, enzymes, dyes and radioactive isotopes. In one embodiment, the detectable marker is a fluorescent dye. In another embodiment, as illustrated in FIG. 6, the detectable marker is a stained particle SP. In one embodiment, the first antibody is a labeled antibody in a freeze-dried state.

In a variation of the embodiment where the first antibody in the first antibody region 22 is labeled with a detectable marker, the device further includes a filtering region 25 which places the first antibody region 22 and test region 28 in fluid connection. The filtering region 25 includes the first antibody, unlabeled. In this embodiment, the first unlabeled antibody serves to bind to free IGFBP-1 in the sample which migrates out of the first antibody region 22 to the filtering region 25 without being bound to the first labeled antibody. Use of a filtering region serves to slow the migration of free IGFBP-1 in the device which did not bind to the first antibody in the first antibody region 22. As a result, free IGFBP-1 which did not bind to the labeled first antibody in the first antibody region 22 does not reach the test region 28 before the labeled first antibody-free IGFBP-1 complex and saturate the binding sites in the test region 28 for the first antibody which otherwise could interfere the immobilization of the labeled first antibody-free IGFBP-1 complex in the test region 28.

In another embodiment of the device, also embodied within the device illustrated in FIGS. 3–9, the device has a strip-like body having proximal and distal ends. A first antibody region 22 of the strip-like body is formed of a material which permits migration of antibodies and proteins therethrough. The first antibody region 22 includes a first antibody which has a binding affinity for free IGFBP-1, introduction to the first antibody region 22 of a fluid sample containing free IGFBP-1 resulting in the attachment of the first antibody to free IGFBP-1 to form a first antibody-free IGFBP-1 complex.

The strip-like body also includes a test region 28 which is distal to the first antibody region 22 and in fluid connection with the first antibody region 22. The test region 28 is formed of a material which permits migration of antibodies and proteins therethrough. The test region 28 includes a second antibody immobilized in the test region 28 which has a binding affinity for free IGFBP-1, the introduction of the fluid sample to the first antibody region 22 resulting in the migration of the first antibody-free IGFBP-1 complex into the test region 28 where the first antibody-free IGFBP-1 complex binds to the second antibody and is immobilized in the test region 28 by the second antibody. The device detects free IGFBP-1 in a sample based on the immobilization of the first antibody in the test region 28.

According to this embodiment, at least one of the first and second antibodies is an antibody according to the present invention. As a result, only free-IGFBP-1 forms a first antibody-IGFBP-1-second antibody complex which is immobilized in the test region 28. As a result, the presence of the first antibody immobilized in the test region 28 is indicative of the presence of free IGFBP-1 in the sample. In one embodiment, the first antibody is an antibody according to the present invention and in another embodiment, the second antibody is an antibody according to the present invention. In a preferred embodiment, both the first and second antibodies are antibodies according to the present invention.

In a variation of the device, the first antibody includes a detectable marker which is used to detect free IGFBP-1 immobilized in the test region 28 by the marker's presence in the test region 28. Examples of detectable markers which may be used include, but are not limited to stained particles, enzymes, dyes and radioactive isotopes. In one embodiment, the detectable marker is a fluorescent dye and in another embodiment, illustrated in FIG. 6, a stained particle having an average dimension between about 20 nm and 40 nm. In one embodiment, the first antibody is a labeled antibody in a freeze-dried state.

In a variation of the embodiment where the first antibody in the first antibody region 22 is labeled with a detectable marker, the device further includes a filtering region 25 which places the first antibody region 22 and test region 28 in fluid connection. The filtering region 25 includes the first antibody, unlabeled. In this embodiment, the first unlabeled antibody serves to bind to free IGFBP-1 in the sample which migrates out of the first antibody region 22 to the filtering region 25 without being bound to the first labeled antibody.

2. Devices with One or More Control Regions

In alternate embodiments of the device, also embodied in the device illustrated in FIGS. 3–9, the device includes one or more control regions. These control regions serve to confirm the proper operation of the device and can also be used to provide a qualitative indication of the relative concentration of free IGFBP-1 in the sample. Examples of devices with one or more control regions are described in this section. It should be noted, however, that alternative control region designs may also be used with the devices of the present invention.

As in the case of devices without control regions, devices with one or more control regions include a first antibody region 22 formed of a material which permits migration of antibodies and proteins therethrough, the first antibody region 22 including a first antibody which has a binding affinity for free IGFBP-1, introduction to the first antibody region 22 of a fluid sample containing free IGFBP-1 resulting in the first antibody binding to free IGFBP-1 to form a first antibody-free IGFBP-1 complex. The device also includes a test region 28 in fluid connection with the first antibody region 22 which is formed of a material which permits migration of antibodies and proteins therethrough. The test region 28 also includes a second antibody immobilized in the test region 28 which has a binding affinity for free IGFBP-1. The second antibody is immunologically distinct from the first antibody such that the first and second antibodies can simultaneously bind to free IGFBP-1. Introduction of the fluid sample to the first antibody region 22 results in the migration of the first antibody-free IGFBP-1 complex into the test region 28 where the first antibody-free IGFBP-1 complex binds to the second antibody and is immobilized in the test region 28 by the second antibody. The device detects free IGFBP-1 in a sample based on the immobilization of the first antibody in the test region 28.

In one variation of this embodiment, the device includes a first control region 30 in fluid connection with the first antibody region 22 formed of a material which permits migration of antibodies and proteins therethrough. The first control region 30 includes free IGFBP-1 immobilized therein. The introduction of the fluid sample to the first region 22 results in the migration of the first antibody which does not form a first antibody-free IGFBP-1 complex in the first antibody region 22 into the first control region 30 where the first antibody binds to the free IGFBP-1 immobilized in the first control region 30. The presence of the first antibody immobilized in the first control region 30 can be used to confirm the proper functioning of the device by detecting the migration of unbound first antibody into the region. The first control region 30 can also be used to detect a low concentration of free IGFBP-1 in the sample based on the amount of first antibody that migrates from the first antibody region 22 without binding to free IGFBP-1.

In another variation of this embodiment, the device includes a second control region 32 in fluid connection with the first antibody region 22 formed of a material which permits migration of antibodies and proteins therethrough. The second control region 32 includes the second antibody immobilized therein. The introduction of the fluid sample to the first region 22 results in the formation of a first antibody-free IGFBP-1 complex which migrates into the second control region 32 where the first antibody-free IGFBP-1 complex binds to the second antibody immobilized in the second control region 32. It is noted that the second control region in this embodiment has the same operation as test region 28.

It is noted that the first and second control regions in this embodiment can be used alone or in combination in the devices of the present invention. When used in combination, the first control region can be used give a positive result when a relatively low concentration of free IGFBP-1 is present in the sample while the second control region can be used to give a positive result when a higher concentration of free IGFBP-1 is present in the sample. Thus, by using a combination of first and second control regions, a positive result is produced by the control regions confirming the proper functioning of the device regardless of the concentration of free IGFBP-1 in the sample.

In another variation of the device, the first control region 30 includes free IGFBP-1 that is not immobilized therein. The device also includes a second control region 32 in fluid connection with the first antibody region 22 formed of a material which permits migration of antibodies and proteins therethrough. The second control region 32 also includes the second antibody immobilized therein.

In this variation, when free IGFBP-1 is present in the sample, the introduction of the fluid sample to the first region 22 results in the formation of a first antibody-free IGFBP-1 complex which migrates into the second control region 32 where the first antibody-free IGFBP-1 complex binds to the second antibody immobilized in the second control region 32. Meanwhile, when a lower concentration of free IGFBP-1 is present in the sample, at least some of the first antibody migrates from the first antibody region 22 to the first control region 30 without forming a first antibody-free IGFBP-1 complex. In the first control region 30, the first antibody binds to free IGFBP-1 present in that region to form a first antibody-free IGFBP-1 complex. The first antibody-free IGFBP-1 complex formed in the first control region 30 then migrates to the second control region 32 where the first antibody-free IGFBP-1 complex binds to the second antibody immobilized in the second control region 32. In this variation, the presence of the first antibody immobilized in the second control region 32 can be used to confirm the proper functioning of the device by detecting the formation of a first antibody-free IGFBP-1-second antibody complex in the second control region 32. In this embodiment, the second control region confirms the proper functioning of the device regardless of the concentration of free IGFBP-1 in the sample through the operation of the first control region 30 to provide free IGFBP-1 when only a low concentration of free IGFBP-1 is present in the sample.

In a variation of the above-described devices which include a first control region, a substance other than free IGFBP-1 can be used in the first control region which binds to the first antibody. For example, instead of using free IGFBP-1, an anti-antibody which is capable of binding to the first antibody can be used in the first control region.

In a variation of the above-described devices which include one or more control regions, the first antibody in the first antibody region 22 includes a detectable marker which is used to detect free IGFBP-1 immobilized in the test region 28 by the marker's presence in the test region 28. The detectable marker may also be used to detect the presence of the labeled first antibody in the first and/or second control regions 30, 32. Examples of detectable markers which may be used include, but are not limited to stained particles, enzymes, dyes and radioactive isotopes. In one embodiment, the detectable marker is a fluorescent dye. In another embodiment, illustrated in FIG. 6, the detectable marker is a stained particle SP. In one embodiment, the first antibody is a labeled antibody in a freeze-dried state.

In a variation of the embodiment where the first antibody in the first antibody region 22 is labeled with a detectable marker, the device further includes a filtering region 25 which places the first antibody region 22 and test region 28 in fluid connection. The filtering region 25 includes the first antibody, unlabeled. In this embodiment, the first unlabeled antibody serves to bind to free IGFBP-1 in the sample which migrates out of the first antibody region 22 to the filtering region 25 without being bound to the first labeled antibody.

Further according to this variation, the device may also include a second filtering region 27 which places the first antibody region 22 in fluid connection with one or more control regions (30 and/or 32). The second filtering region 27 includes the first antibody, unlabeled. The first unlabeled antibody serves to bind to free IGFBP-1 in the sample which migrates out of the first antibody region 22 to the second filtering region 27 without being bound to the first labeled antibody.

Use of a filtering region serves to slow the migration of free IGFBP-1 in the device which did not bind to the first antibody in the first antibody region 22. As a result, free IGFBP-1 which did not bind to the first antibody in the first antibody region 22 does not reach the test region 28 (or the second control region 32) and saturate the binding sites in the test region 28 (and second control region 32) for the first antibody-free IGFBP-1 complex.

In another variation of the devices of the present invention which include a control region, the test region and control region are designed relative to each other so that a greater percentage of the sample is migrates into the test region 28 than into the control region.

In a more specific example of a device according to the present invention, the device includes:

a first antibody region 22 containing a first monoclonal antibody which has a binding affinity for free IGFBP-1, introduction of a fluid sample containing free IGFBP-1 to a porous sample application matrix 42 within the first antibody region 22 resulting in the first antibody binding to free IGFBP-1 to form a first antibody-free IGFBP-1 complex;

a porous test matrix 28 in fluid connection with the porous sample application matrix 42 and the first antibody region 22, the porous test matrix containing a second monoclonal antibody coupled to the test matrix which has a binding affinity for free IGFBP-1; and a porous control matrix containing
  i) a first control region 30 having free IGFBP-1 attached thereto; and
  ii) a second control region 32 having the second monoclonal antibody attached thereto, the control matrix being in fluid connection with the sample application matrix 42 and the first antibody region 22 such that sample migrates from sample application matrix 42 to and through the first control region 30 to the second control region 32.

According to this embodiment, at least one of the first and second antibodies is an antibody according to the present invention. As a result, only free-IGFBP-1 forms a first antibody-IGFBP-1-second antibody complex which is immobilized in the porous test matrix 28. Hence, the presence of the first antibody in the porous test matrix 28 is indicative of the presence of free IGFBP-1 in the sample. In one embodiment, the first antibody is an antibody according to the present invention and in another embodiment, the second antibody is an antibody according to the present invention. In a preferred embodiment, both antibodies are antibodies according to the present invention. Further according to this embodiment, the first antibody optionally includes a detectable marker which is used to detect free IGFBP-1 immobilized in the porous test matrix 28 by the marker's presence in the porous test matrix 28. Examples of detectable markers which may be used include, but are not limited to stained particles, enzymes, dyes and radioactive isotopes. In one embodiment, the detectable marker is a fluorescent dye and in another embodiment a stained particle. In one embodiment, the first antibody is a labeled antibody in a freeze-dried state.

The materials used in the various regions of the above described devices may be any material which permits migration of antibodies and proteins therethrough. Examples of suitable materials include but are not limited to fiberglass, porous plastic, nitrocellulose, and filter paper.

The above-described devices may optionally include a protective film covering at least a portion of the device, the film including an aperture for introducing a sample to the device. In one embodiment, the protective film covers the region used to detect the first antibody-free IGFBP-1-second antibody complex and is transparent.

It is noted that the above devices with one or more control regions are described where the control regions are positioned on a fluid path that is independent of the test region. However, as described in Example 6 and illustrated in FIG. 11, one or more control regions may also be positioned on the same fluid path as the test region.

B. Methods for Detecting Free IGFBP-1

Embodiments of methods for detecting free IGFBP-1 according to the present invention are described below.

In one embodiment of the method, free IGFBP-1 is detected in a sample by contacting a sample containing free IGFBP-1 with an antibody according to the present invention to form an antibody-free IGFBP-1 complex. The antibody-free IGFBP-1 complex is then detected. In one variation of this embodiment, the antibody includes a detectable marker, the step of detecting the antibody-free IGFBP-1 complex including detecting the detectable marker.

In another embodiment of the method, free IGFBP-1 is detected in a sample by contacting the sample with a first antibody which has a binding affinity for free IGFBP-1, the antibody forming a first antibody-free IGFBP-1 complex. The sample is then contacted with a second antibody having a binding affinity for free IGFBP-1. The second antibody is immunologically distinct from the first antibody such that the first and second antibodies can simultaneously bind to free IGFBP-1 The second antibody binds to the first antibody-free IGFBP-1 complex to form a first antibody-free IGFBP-1-second antibody complex. Free IGFBP-1 is detected by detecting the first antibody-free IGFBP-1-second antibody complex. According to this embodiment of the method, at least one of the first and second antibodies is an antibody according to the present invention. As a result, only free-IGFBP-1 forms a first antibody-free IGFBP-1-second antibody complex. This enables one to detect the presence of free IGFBP-1 based on the presence of the first antibody. In one embodiment, the first antibody is an antibody according to the present invention and in another embodiment, the second antibody is an antibody according to the present invention. In a preferred embodiment, both the first and second antibodies are antibodies according to the present invention.

In a further variation of this method, the second antibody is bound to a solid support, the step of detecting the first antibody-free IGFBP-1-second antibody complex including immobilizing the first antibody-free IGFBP-1-second antibody complex on the solid support and detecting the immobilized first antibody-free IGFBP-1-second antibody complex.

When the above-described methods include using a first antibody which is labeled with a detectable marker, a variation of the method includes, prior to contacting the sample with the second antibody, contacting the sample with the first antibody, unlabeled. In this variation, the unlabeled first antibody serves to bind to free IGFBP-1 in the sample which did not bind to the labeled first antibody. This additional step serves to insure that the mobility of all free IGFBP-1 in the sample is comparable by insuring that all free IGFBP-1 in the sample are bound to some form of the first antibody.

Another embodiment of the method includes the steps of: adding a sample to a first antibody region of material which permits migration of antibodies and proteins therethrough, the first antibody region including a first antibody which has a binding affinity for free IGFBP-1, introduction to the first antibody region of a fluid sample containing IGFBP-1 free of IGF-1 and IGF-2 resulting in the attachment of the first antibody to free IGFBP-1 to form a first antibody-free IGFBP-1 complex;

migrating the sample to a test region of material, the test region containing a second antibody immobilized therein which has a binding affinity for free IGFBP-1, migration of the sample to the test region resulting in the second antibody binding to the first antibody-free IGFBP-1 complex to form an immobilized first antibody-free IGFBP-1-second antibody complex; and detecting the immobilized first antibody-free IGFBP-1-second antibody complex in the test region.

A further variation of the above method further includes the steps of:

migrating the first antibody from the first region to a first control region of material, the first control region containing free IGFBP-1 bound thereto, migration of the sample to the first control region resulting in first antibody forming an immobilized first antibody-free IGFBP-1 complex in the first control region; and detecting the immobilized first antibody-free IGFBP-1 complex in the first control region, the presence of the complex in the first control region indicating a low concentration of free IGFBP-1 in the sample.

In a variation of the method where the first antibody in the first antibody region is labeled with a detectable marker, the first antibody region and test region of material may be connected to each other through a first filtering region formed of a material which permits the migration of antibodies and proteins therethrough. In this variation, the step of migrating the sample from the first antibody region to the test region includes migrating the sample from the first antibody region through the first filtering region to the test region. According to this variation, the first filtering region includes the first antibody unlabeled, the method including the step of binding the first unlabeled antibody to free IGFBP-1 in the sample which did not bind to the first labeled antibody during migration of the sample through the first antibody region. Further according to this variation, the first antibody region and control region may also be connected to each other through a filtering region formed of a material which permits the migration of antibodies and proteins therethrough. In this variation, the step of migrating the sample from the first antibody region to the control region includes migrating the sample from the first antibody region through a second filtering region to the control region. According to this variation, the second filtering region includes the first antibody unlabeled, the method including the step of binding the first unlabeled antibody to free IGFBP-1 in the sample which did not bind to the first labeled antibody during migration of the sample through the first antibody region.

According to the above-described methods, the first antibody may include a detectable marker, the step of detecting the free IGFBP-1 complex including detecting the detectable marker. Examples of detectable markers that can be used include stained particles, enzymes, dyes and radioactive isotopes. In a preferred embodiment, the detectable marker is a fluorescent dye or a stained particle, preferably having an average dimension between about 20 nm and 40 nm.

C. Methods and Devices for Detecting Fetal Membrane Ruptures

The present invention also provides methods and devices for detecting a rupture in a fetal membrane based on the presence of free IGFBP-1 in the vaginal fluid of a pregnant woman. In its broadest sense, the method of the present invention for detecting fetal membrane ruptures simply includes the step of detecting free IGFBP-1 in a vaginal secretion, the presence of free IGFBP-1 in a vaginal secretion indicating the occurrence of a fetal membrane rupture.

Applicants were the first to identify that free IGFBP-1 occurs in amniotic fluid in significantly higher concentrations than in serum. It is the realization of the significant difference in the concentration of free IGFBP-1 in amniotic fluid and in serum which enables the detection of amniotic fluid in a vaginal secretion based on the presence of free IGFBP-1 in the secretion. Because it was known that the presence of amniotic fluid in a vaginal secretion is indicative of a fetal membrane rupture, the detection of free IGFBP-1 in a vaginal secretion can also be used to detect the presence of a fetal membrane rupture.

Examples of methods and devices for detecting free IGFBP-1 in a vaginal secretion include the methods and devices described above in Sections VII (A) and (B), the methods further including the step of detecting a fetal membrane rupture based on the detection of free IGFBP-1 in the sample. It should be noted, however, that the present method for detecting the presence of a fetal membrane rupture can incorporate other methods for detecting free IGFBP-1 in a vaginal secretion, such as the electrophoretic separation and detection of free IGFBP-1.

As has been discussed above, methods and devices according to the present invention for detecting fetal membrane ruptures are highly sensitive and accurate. For example, concentrations of 5 ng/mL free IGFBP-1 and lower can be detected according to the present invention. Because the average concentration of free IGFBP-1 in serum is only about 21 ng/mL, as compared to an average concentration of about 25,000 ng/mL in amniotic fluid, a low detection limit for the free IGFBP-1 can be used in the method of the present invention for detecting the occurrence of a fetal membrane rupture without a high number of false negative results. In addition, fetal membrane ruptures can be detected at an earlier stage according to the present invention than by prior methods and devices. The methods and devices are also designed to avoid producing false positive results through the use of antibodies which are highly specific for IGFBP-1. As a result, the methods and devices are not influenced by the presence of vaginal infections or other variables which have reduced the accuracy of prior methods for detecting fetal membrane ruptures. In addition, the large ratio between serum and amniotic free IGFBP-1 makes the methods and devices significantly less likely to produce false positive results due to the presence of serum in vaginal secretions, even when a low free IGFBP-1 detection limit is used.

The devices and methods of the present invention are also designed to be easily used in a rapid and convenient manner, thereby making it possible to for these methods and devices to be used on an outpatient basis. For example, the method can be incorporated into an easy-to-use device which can be operated by a patient with little or no prior experience with the device. No special timing, dilution or matching of the sample concentrations prior to measurement is required in order to perform the method or use the device. This makes the methods and devices of the present invention for detecting fetal membrane ruptures highly reliable and not highly susceptible to operator error. The methods and devices are also simple and inexpensive and does not require any expensive instrumentation to perform.

VIII. Devices & Methods for Detecting a Biomolecule with Two Binding Sites

The present invention also relates to devices and methods for detecting a biomolecule in a sample which has two distinct binding sites using two different antibodies which selectively bind to the two binding sites. Examples of these devices and methods are described in detail in Sections VII (A) and (B) with regard to the detection of free IGFBP-1. Although the methods and devices described in Sections VII (A) and (B) are directed to detecting free IGFBP-1, it should be noted that these devices and methods can be readily adapted for detecting any biomolecule which has two distinct binding sites for which two different antibodies are known. Examples of such biomolecules include but are not limited to proteins, particularly carrier proteins, lipids, sugars, glycolipids and the like.

The following examples describe in further detail the isolation of free IGFBP-1 from amniotic fluid, the generation of antibodies against free IGFBP-1, and the screening of such antibodies. These examples are provided to illustrate the certain aspects of the invention and are not intended to limit the scope of the present invention. Still further objects and advantages will become apparent upon consideration of the ensuing description with reference to the accompanying drawings.

EXAMPLES

1. Materials and Methods

The following methods and materials were used in the examples which are described herein.

A. ISOLATION OF PROTEIN FROM AMNIOTIC FLUID

IGFBP-1 was isolated from amniotic fluid obtained from the obstetrical clinic of the Child and Mother Health Care Center (Moscow), and was purified and characterized according to standard methods known in the art (Boltovskaya, U., et al., *Bull. Exp. Biol. and Med.* (Russia) Vol. 10:397–400 (1991)).

An example of a procedure which may be used to isolate IGFBP-1 from amniotic fluid will now be described. First, up to 0.3% a $LaCl_3$ solution is added to an amniotic fluid sample at 4° C. The resulting solution is then incubated at 4° C. for 4 hours. After incubation, the resulting solution is centrifuged and the supernatant isolated. The supernatant is then precipitated by adding $(NH_4)_2SO_4$ to a concentration of up to 50% of saturation and incubating the resulting solution at 4° C. for 36 hours. The precipitate is then dissolved using a volume of distilled water 10 times in excess of the initial volume of amniotic fluid.

The proteins dissolved from the precipitate are then separated by hydrophobic chromatography using octyl-"SEPHAROSE" (beaded agarose) eluted with a 50% ethylene glycol solution. The eluted proteins are detected by spectrophotometric measurement at 280 nm. After purification by hydrophobic chromatography, the eluate is further purified by dialysis against distilled water at 4° C. for 12 hours. A study of the resulting IGFBP-1 concentration in the eluate after dialysis may be performed by an immuno migration technique using standard IGFBP-1 and polyclonal anti-IGFBP-1 antibodies.

The proteins including IGFBP-1 present in the eluate after dialysis may be freeze dried. Further analysis of IGFBP-1 can be performed by electrophoresis in polyacrylamide gel and immunoblotting of IGFBP-1 using nitrocellulose and the following proteins as standards: bovine serum albumin (Serva, Germany), 67 kD; egg albumin (Serva, Germany), 43 kD; carbonic anhydrase (Serva, Germany), 30 kD; lactalbumin, (Serva, Germany), 14.4 kD; and cytochrome C, (Serva, Germany) 12.5 kD.

B. IDENTIFICATION OF PROTEIN BY IMMUNOBLOTTING

The molecular weight and immunological features of the isolated protein were determined by PAGE (polyacrylamide gel electrophoresis) and immunoblotting (Boltovskya, et al., 1991), utilizing rabbit polyclonal and murine monoclonal antibodies to IGFBP-1 which are described in Boltovskaya, U., et al., *Bull. Exp. Biol. and Med.* (Russia) Vol. 10:397–400 (1991) and a panel of standard proteins (bovine serum albumin, 67 kD, egg albumin, 43 kD, chymotrypsinogen A, 25 kD, and IGFBP-1, 35 kD).

Purified IGFBP-1 was suspended in Freund's adjuvant (Pierce) and the resulting antigen preparation was used in subsequent immunizations.

2. Production of Monoclonal Antibodies

The following procedure was used to produce and identify antibodies with a binding affinity according to the present invention.

A. IMMUNIZATION AND PRODUCTION OF MONOCLONAL ANTIBODIES

1. Immunization: Six Balb/c mice were immunized intraperitoneally (3 mice) or into foot pads (3 mice) with IGFBP-1 (obtained as described in Example 1) according to a standard immunization protocol (Harlow, E., and Lane, D., in *ANTIBODIES A LABORATORY MANUAL*, Cold Spring Harbor Laboratory, 1988, pages 151, 156–159).

2. Cell Fusion: Spleens and inguinal lymph nodes were removed, the spleen and lymph-node B-cells were collected, and fused with Sp2/0 myeloma cells using polyethylene glycol (Merck 4000) as fusogen (Kohler, G. and Milstein., C., *Eur. J. Immunol.*, 6:511–519 (1976); Harlow, E., and Lane, D., in *ANTIBODIES A LABORATORY MANUAL*, Cold Spring Harbor Laboratory, 1988, pages 143–144).

3. Production of Hybridomas: Hybridomas were selected by growth in HAT selection medium (Littlefield, J. W., *Science* 145:709 (1964)); Harlow, E., and Lane, D., in *ANTIBODIES A LABORATORY MANUAL*, Cold Spring Harbor Laboratory, 1988, p. 204), according to standard methods (Galfre, G., and Milstein, C., *Methods in Enzymol.* 73:3–46 (1981)). Out of approximately 1500 wells each seeded with $10^4$ cells, 500 wells contained viable hybridomas.

B. Screening of Hybridoma Supernatants for Production of Antibodies

1. Detection of Monoclonal Antibodies to IGFBP-1.

Samples of tissue culture media were removed from each of the 500 wells containing viable hybridomas, and the supernatants were tested for the presence of monoclonal antibodies immunoreactive with IGFBP-1 according to a routine antibody capture ELISA protocol utilizing purified IGFBP-1 antigen bound to a solid phase (Catt, K., and Tregear, G. W., *Science* 153: 1570–1572 (1967); Salmon, S. E., et al., *J. Immunol.* 103:129–137 (1969); Engvall, E. and Perlmann, P., *J. Immunol.* 109:129–135 (1972)).

Standard 96-well plates were coated with polyclonal rabbit antibodies to IGFBP-1 (0.1 mL, 0.01 mg/mL) in carbonate-bicarbonate buffer, 0.05M) at pH 9.6 and incubated for 18 hours at 37° C. The plates were then washed three times with a PBS (phosphate buffered saline) solution composed of phosphate-buffered saline (pH 7.4) containing 0.05% TWEEN 20™ (polyoxyethylenesorbitan monolaurate). Non-specific binding activity was blocked by addition of 0.1% bovine serum albumin in PBS (0.1 mL) to each well. Subsequent to the addition of the blocking agent, the plates were incubated for 1 hour at 37° C., followed by three washings with PBS solution. IGFBP-1 in PBS solution (0.1 mL) was then added to each well, and the plates were incubated at 37° C. for 2 hours, followed by three washings with PBS. To each well was added 0.1 mL of hybridoma cell supernatant, and the plates were then incubated for one hour at 37° C., followed by washing three times with PBS solution. A solution of peroxidase-antimouse IgG (diluted 1/1000, 0.1 mL) was then added to each well, and the plates were incubated for 1 hour at 37° C., and then washed five times with PBS solution. Peroxidase activity was developed by addition of 0.1 mL of o-phenylenediamine solution (0.5 mg/mL) in 0.05 citrate buffer (pH 7.4) containing 0.03% hydrogen peroxide, followed by incubation for 30 minutes at room temperature. A stop solution containing 0.05 mL of 1N sulfuric acid was then added to each well. Optical density of each of the cells was measured using a Titertec-Multiscan spectrophotometer at a wavelength of 492 nm to detect positive binding. Of the 500 hybridoma supernatants screened for production of monoclonal antibodies, 9 cultures produced antibodies that were immunoreactive with IGFBP-1.

2. Selection of Monoclonal Antibodies Which Compete with IGF-1 and IGF-2 And Competitive Binding Study Competitive ELISA sandwich assays were carried out to determine the extent of cross-reactivity between newly isolated monoclonal antibodies, MAb-1 or MAb-2, with both IGF-1 and IGF-2.

A. EXPERIMENT 1A: INHIBITION OF MAb-1 BINDING

MAb-2 (10 µg/mL) was adsorbed on standard 96-well plates plate wells. A solution of IGFBP-1 (20 ng/mL) was added to each well. The plate was incubated for 1 hour at 37° C., using a shaker. After intensive washing of the plate wells, human IGF-1 (200 ng/mL, Calbiochem.), or IGF-2 (1 mg/mL, Calbiochem.) was added to the different wells. Following 12 hours of incubation at 4° C. and intensive washing of the wells, a conjugate of MAb-1 with horseradish peroxidase was added to each well. The wells were incubated for 1 hour at room temperature, followed by intensive washing with phosphate buffered saline. A solution of orthophenylendiamine and $H_2O_2$ was then added to each well and the intensity of staining was measured spectrophotometrically, as described above.

B. EXPERIMENT 1B: INHIBITION OF MAb-2 BINDING

MAb-1 (10 µg/mL) was adsorbed on standard 96-well plates plate wells. A solution of IGFBP-1 (20 ng/mL) was added to each well. The plate was incubated for 1 hour at 37° C., using a shaker. After intensive washing of the plate wells, human IGF-1 (200 ng/mL, Calbiochem.), or IGF-2 (1 mg/mL, Calbiochem.) was added to the different wells. Following 12 hours of incubation at 4° C. and intensive washing of the wells, a conjugate of MAb-2 with horse radish peroxidase was added to each well. The wells were incubated for 1 hour at room temperature, followed by intensive washing with phosphate buffered saline. A solution of orthophenylendiamine and $H_2O_2$ was then added to each well and the intensity of staining was measured spectrophotometrically, as described above.

C. EXPERIMENT 2A

The assay procedure described above for experiment 1a was repeated, with the following exception. Subsequent to addition of IGFBP-1 solution, to each of the wells was added either 5 µg/mL of human IGF-1, or 500 µg/mL of human IGF-2, followed by incubation at 37° C. for 2 hours.

D. EXPERIMENT 2B

The assay procedure described above for experiment 1b was repeated, with the following exception. Subsequent to addition of IGFBP-1 solution, to each of the wells was added either 5 µg/mL of human IGF-1, or 500 µg/mL of human IGF-2, followed by incubation at 37° C. for 2 hours.

Controls were carried out for each of the above sets of experiments. In each set of control experiments, the second well layer, i.e., IGFBP-1, was omitted from the assay procedure. The concentration of IGF-1 ranged from 0–5 µg/mL, while the concentration of IGF-2 was varied from 0–500 µg/mL.

The conditions for Experiments 1a–1b and 2a–2b are summarized in Table 1 below. The percentage of binding inhibition of MAb-1 or MAb-2 to IGFBP-1 by either IGF-1 or IGF-2 is summarized in Table 2 below. Meanwhile, FIG. 10 is a plot showing the concentration of MAb-1 and MAb-2 versus the concentration of IGF-2 at which 56% inhibition of MAb-1 and 100% inhibition of MAb-2 occurs.

TABLE 1

SANDWICH ASSAY CONDITIONS

| Layer | Expt. 1a | Expt. 1b | Expt. 2a | Expt. 2b |
|---|---|---|---|---|
| Bottom | MAb-2, 10 ng/mL | MAb-1, 10 ng/mL | MAb-2 | MAb-1 |
| 2nd | IGFBP-1, 20 ng/mL | IGFBP-1, 20 ng/mL | IGFBP-1, 20 ng/mL | IGFBP-1, 20 ng/mL |
| 3rd | IGF-1, 200 ng/mL or IGF-2, 1 µg/mL | IGF-1, 200 ng/mL or IGF-2, 1 µg/mL | IGF-1, 5 µg/mL or IGF-2, 500 µg/mL*** | IGF-1, 5 µg/mL or IGF-2, 500 µg/mL*** |
| 4th | MAb-1** | MAb-2** | MAb-1** | MAb-2** |

*for 12 hours at 4° C.
**conjugated with Horse Radish Peroxidase
***for 2 hours at 37° C.

TABLE 2

COMPETITIVE BINDING RESULTS

| MAbs | N exp. | IGF-1 Concentration | Inhibition % | IGF-2 Concentration | Inhibition % |
|---|---|---|---|---|---|
| MAb-1 | 1a | 200 ng/mL | 45 | 1 µg/mL | 49 |
|  | 2a | 5 µg/mL | 82 | 500 µg/mL | 56.3 |
| MAb-2 | 1b | 200 ng/mL | 40 | 1 µg/mL | 69 |
|  | 2b | 5 µg/mL | 81.5 | 500 µg/mL | 100 |

The findings shown in Table 2 and illustrated in FIG. 10 indicate that IGF-1 inhibits binding of MAb-1 to IGFBP-1 by approximately 45–82%, while MAb-2 binding to IGFBP-1 is inhibited in the presence of IGF-1 by about 40–81%. IGF-2 was found to inhibit binding of MAb-1 to IGFBP-1 by approximately 49–56%, and of MAb-2 by about 69–100%.

3. Determination of Concentration of Free IGFBP-1 in Fluids

In this section, the determination of the concentrations of free IGFBP-1 both in serum and in the amniotic fluid is described. These concentrations were measured using monoclonal antibodies MAb-1 and MAb-2. It is also noted that the concentration can be measured using any method known in the art of immunochemistry. One such method, known as ELISA, was used by Boltovskaya et al. for measuring IGFBP-1. *Bull Exp. Biol. Med.*, 1991, No. 10, pp. 397–400.

Table 3 shows the concentration of free IGFBP-1 in the sera of a series of pregnant women. The measurements presented in Table 3 were obtained using the ELISA procedure. As can be seen from the data presented in Table 3, during the second and third trimesters of pregnancy, the highest concentration of free IGFBP-1 in the sera of women with an uncomplicated pregnancy was equal to about 35 ng/mL, with an average value of about 21 ng/mL.

Table 4 shows the concentration of free IGFBP-1 in amniotic fluid during the second and third trimesters of pregnancy as tested in 47 pregnant women. As can be seen from Table 4, the concentration of free IGFBP-1 ranged from 1000 to 250,000 ng/mL with an average of about 25,742 and a standard deviation of about 6604. As can be seen from this data, the concentration of free IGFBP-1 in amniotic fluid is about 1000 times greater than in the sera of the patients tested. Further, in only 8% of all patients studied was the concentration of free IGFBP-1 4000 ng/mL or lower.

TABLE 3

CONCENTRATION OF FREE IGFBP-1 IN THE SERA OF PREGNANT WOMEN (NG/ML)

| Second Trimester (13–25 Weeks of Gestation) | | | | Third Trimester (26–40 Weeks of Gestation) | | | |
|---|---|---|---|---|---|---|---|
| 24 | 17 | 35 | 25 | 15 | 40 | 6 | 28 | 25 |
| 19 | 15 | 10 | 19 | 21 | 15 | 42 | 32 | 27 |
| 30 | 10 | 39 | 15 | 12 | 11 | 31 | 24 | 40 |
| 25 | 12 | 46 | 5 | 11 | 38 | 40 | 22 | 35 |
| 14 | 22 | 22 | 7 | 30 | 25 | 30 | 17 | 25 |
| 14 | 31 | 27 | 19 | 3 | 12 | 32 | 13 | 26 |
| 27 | 13 | 27 | 21 | 6 | 33 | 30 | 15 | 20 |
| 8 | 38 | 36 | 12 | 12 | 31 | 41 | 12 | 23 |
| 19 | 31 | 12 | 9 | 20 | 40 | 13 | 20 | 35 |
| 15 | 20 | 39 | 22 | 6 | 24 | 30 | 17 | 17 |
| 16 | 40 | 19 | 13 | 15 | 25 | 17 | 16 | 17 |
| 12 | 18 | 25 | 8 | 3 | 33 | 25 | 8 | 15 |
| 17 | 11 | 35 | 8 | 11 | 17 | 16 | 22 | 12 |
| 17 | 40 | 28 | 19 | 7 | 26 | 14 | 20 | 25 |
| 7 | 27 | 17 | 7 | 17 | 30 | 5 | 10 | 8 |
| 16 | 27 | 20 | 6 | 10 | 14 | 32 | 30 | 32 |
| 7 | 14 | 19 | 5 | 9 | 40 | 40 | 32 | 28 |
|  |  |  | 8 | 10 | 45 |  | 30 | 35 |

N = 55
Range 7–46 ng/mL
M ± m = 21.58 ± 1.33

N = 107
Range 3–45 ng/mL
M ± m = 20.52 ± 1.03

In the above table, N stands for the number of measurements, M is the arithmetic mean, and m is the root-mean-square value.

TABLE 4

CONCENTRATION OF FREE IGFBP-1 IN AMNIOTIC FLUID DURING THE SECOND AND THIRD TRIMESTERS OF GESTATION

| Free IGFBP-1 (ng/mL) | | |
|---|---|---|
| 1680 | 1800 | 1200 |
| 8000 | 26000 | 8000 |
| 6000 | 25000 | 30000 |
| 1000 | 20000 | 6000 |
| 1200 | 100000 | 1000 |
| 20000 | 5000 | 12000 |
| 1000 | 4500 | 20000 |
| 8000 | 12000 | 4000 |
| 250000 | 30000 | 10000 |
| 12000 | 12500 | 7000 |
| 25000 | 25000 | 180000 |
| 6000 | 50000 |  |
| 15000 | 80000 |  |
| 27000 | 9000 |  |
| 5200 | 40000 |  |
| 10000 | 41000 |  |
| 12000 | 8000 |  |
| 4000 | 8000 |  |

N = 47
Range 1000–250000
M ± m = 25742 ± 6604.6

N, M and m are the same as defined above.

The large difference in the concentration of free IGFBP-1 in amniotic fluid and serum enables the detection of very low concentrations of free IGFBP-1 of amniotic origin (5–10 ng/mL) in vaginal secretions. By being able to detect such low concentrations of amniotic free IGFBP-1 in vaginal secretions, it is possible to detect fetal membrane ruptures based on the presence of free IGFBP-1 in a sample.

One important advantage associated with detecting fetal membrane ruptures based on an increased level of free IGFBP-1 in vaginal secretions as compared to serum is that false positive results are not obtained if the fetal membrane has not ruptured. This is one of the important advantages of the method of the present invention, because the primary problem in diagnosing the rupture of fetal membranes is to distinguish small amounts of the amniotic fluids from other body fluids which may be present in the vagina.

4. ELISA Study of Mutual Inhibition of MAb-1 and MAb-2 Binding to IGFBP-1

Details of the ELISA screening protocol used to determine the cross-reactivity between monoclonal antibodies MAb-1, MAb-2, MAb-4, MAb-5 and MAb-7 is provided in Table 5 below. The concentrations of the horse radish peroxidase-monoclonal antibody conjugate solutions were adjusted to obtain 1.0 unit of optical density in direct ELISA, at an IGFBP-1 concentration of 1 µg/mL.

TABLE 5

MUTUAL INHIBITION ASSAY CONDITIONS

| Layer | Assay Conditions |
| --- | --- |
| First (bottom) | one of MAb-1, MAb-2, MAb-4, MAb-5, MAb-7 (1 µg/mL) |
| 2nd | amniotic IGFBP-1 (20 ng/mL) |
| 3rd | horseradish peroxidase conjugate with one of MAb-1, MAb-2, MAb-4, MAb-5, MAb-7 not used in first layer (1 µg/mL) |

TABLE 6

RESULTS OF MUTUAL INHIBITION ELISA

| First Layer Conjugate | MAb-4 | MAb-1 | MAb-5 | MAb-7 | MAb-2 |
| --- | --- | --- | --- | --- | --- |
| MAb-4 | – | – | – | – | +++ |
| MAb-1 | – | – | – | – | ++++ |
| MAb-5 | – | – | – | – | ++ |
| MAb-7 | – | – | – | – | +++ |
| MAb-2 | +++ | +++++ | +++ | ++ | – |

The results of the cross-reactivity evaluation are presented in Table 6. Findings are indicated by the number of "+" entries in each box. A dash "-" indicates an optical density reading of approximately zero (no observation of color). The greatest number of "+" entries, 5, is approximately equivalent to the highest optical density obtained in these experiments (2.0 optical density units at λ=492 nm). Results are normalized relative to this value. Based upon optical density readings, no cross reactivity was observed between MAb-1 and MAb-2. Both MAb-1 and MAb-2, in unlabeled form, inhibited their own respective binding (labeled form) to IGFBP-1.

5. Bidirectional Device for Diagnosing Fetal Membrane Rupture

A preferred embodiment of a device according to the present invention for detecting free IGFBP-1 in a sample which may be used to diagnose fetal membrane ruptures based on the presence of free IGFBP-1 is illustrated in FIGS. 3 and 4. FIG. 3 is a schematic longitudinal sectional view of the device. FIG. 4 is a plan view of the device of FIG. 3, the internal structure of the device being seen through a transparent protective film.

As shown in FIGS. 3 and 4, the device comprises a strip-like body composed of several sequentially interconnected elements. More specifically, a central part of the device comprises a first antibody region 22 which contains MAb-1 labeled with a detectable marker.

First antibody region 22 may be made of a fiberglass tissue. In one specific example, the first antibody region 22 has a thickness of 0.25 mm, a width of 7 mm, and a length of 30 mm. The material of first antibody region 22 is porous and permits the migration of various particles which will be described later. The labeled MAb 1 may be introduced into first antibody region 22, for example, by impregnating the first antibody region 22 with a solution of labeled MAb-1 with subsequent freeze-drying.

In one embodiment, the detectable marker attached to MAb-1 is stained particles SP (not shown in the drawings). One type of stained particles that may be used is gold particles having an average dimension within the range of 20 to 40 nm. To prevent non-reversible binding of the antibody-gold particle conjugate to the glass fiber pad forming the first antibody region 22, the antibody-gold conjugate is preferably dissolved in a solution containing 2% casein and 2% sucrose (Low, et al.) which is introduced into the pad via an automatic pipette. Freeze drying of the pad loaded with labeled antibodies may be accomplished by freezing the pad at a rate of 1° C. per minute to a temperature of −40° C., followed by transferring the pad to a vacuum-freeze dryer, where it is freeze dried for 12 hours at 10° C.

Connected to the opposite ends of the first antibody region 22 in its longitudinal direction are a first nitrocellulose strip 24, which is used to form a test region 28 and a second nitrocellulose strip 26 which is used to form first and second control regions 30, 32.

Located in an intermediate position of nitrocellulose strip 24 is a test region 28 which is arranged transversely to the device over its entire width. Test region 28 is a portion of nitrocellulose material of strip 24 which is impregnated by MAb-2. Nitrocellulose strip 24 may have a thickness of 0.1 mm, a length of 15 mm, and a width of 7 mm. Test region 28 may be located, e.g., at a distance of 5 mm from the end of pad 22, and may have a width of 1 mm.

The second nitrocellulose strip 26 may have the same dimensions as the first nitrocellulose strip 24 and may contain two transverse control regions, i.e., first control region 30 and second control region 32, which also may cross the entire width of nitrocellulose strip 26 and each have the same width as test region 28. The space between the first and second control regions 30 and 32 may be about 1 mm.

Second control region 32 is identical to test region 28 in that it is impregnated by MAb-2. Meanwhile, the first control region 30 is impregnated with free IGFBP-1. The second control region 32 is positioned distal relative to the first control region 30 such that a sample introduced into the first antibody region 22 migrates through the first control region 30 to the second control region 32.

MAb-2 and free IGFBP-1 may be introduced into respective nitrocellulose strips 24 and 26 by a contact or non-contact method, e.g., with the use of a dosing drawing-pen-type contact device where the solution is used instead of ink.

Filter paper strips 34 and 36 are connected to the distal ends of nitrocellulose strips 24 and 26. These strips are identical and may have a thickness of 0.2 mm, a width of 7 mm, and a length of 15 mm. Thus, the overall length of the device according to this embodiment is about 90 mm.

Experimental analysis has shown that a very high concentration of free IGFBP-1 in a sample may decrease the staining of both the testing and control regions. This is because the speed of migration of the concentrated free IGFBP-1 exceeds the speed of migration of free IGFBP connected to labeled MAb-1. To prevent such an effect, filtering regions 25 and 27 containing nonlabeled MAb-1 can be incorporated into nitrocellulose strip 24 and nitrocellulose strip 26 respectively for filtering free IGFBP-1 not bound to the labeled MAb-1. These filtering regions 25 and 27 containing non-labeled MAb-1 are positioned on portions of the lengths of nitrocellulose strips 24 and 26 between first antibody region 22 and test region 28 and between first antibody region 22 and first control region 30.

In order to protect the device from contamination, lateral inflow effect, etc., the entire surface of the device is coated from both sides with protective films 38 and 40. An example of a protective film which may be used is a conventional thin transparent adhesive tape.

An aperture 50 is provided on the front side of the device in protective film 38 for the introduction of a sample of vaginal secretions.

The device may be enclosed in its entirety into a rigid or semirigid casing 44 which closes the front, rear, and sides of the device (with the exception of aperture 42), in order to provide additional mechanical and chemical protection of the device. Casing 44 may be made of plastic such as polycarbonate. For additional clarity of the drawings, casing 44 is shown only in FIG. 3. Casing 44 can be made of transparent or non-transparent plastic. In the event an opaque or semi-transparent plastic is used, casing 44 may be provided with windows 46 and 48 to allow visual observation of conditions of test region 28 and first and second control regions 30 and 32, respectively.

Operation of the device illustrated in FIGS. 3–4 will now be described with reference to FIGS. 3–9 which illustrate the immunochemical interactions which occur within the components of the device during sample analysis.

When it is necessary to test the condition of a patient for the presence of ruptured fetal membranes, a sample of vaginal secretion may be taken by a conventional method. A sample of about 50 $\mu$l to 100 $\mu$l is introduced into the first antibody region 22 through aperture 50. The sample can be introduced by using a pipette, swab, syringe, or any other suitable device (not shown in drawings).

Figure 5:
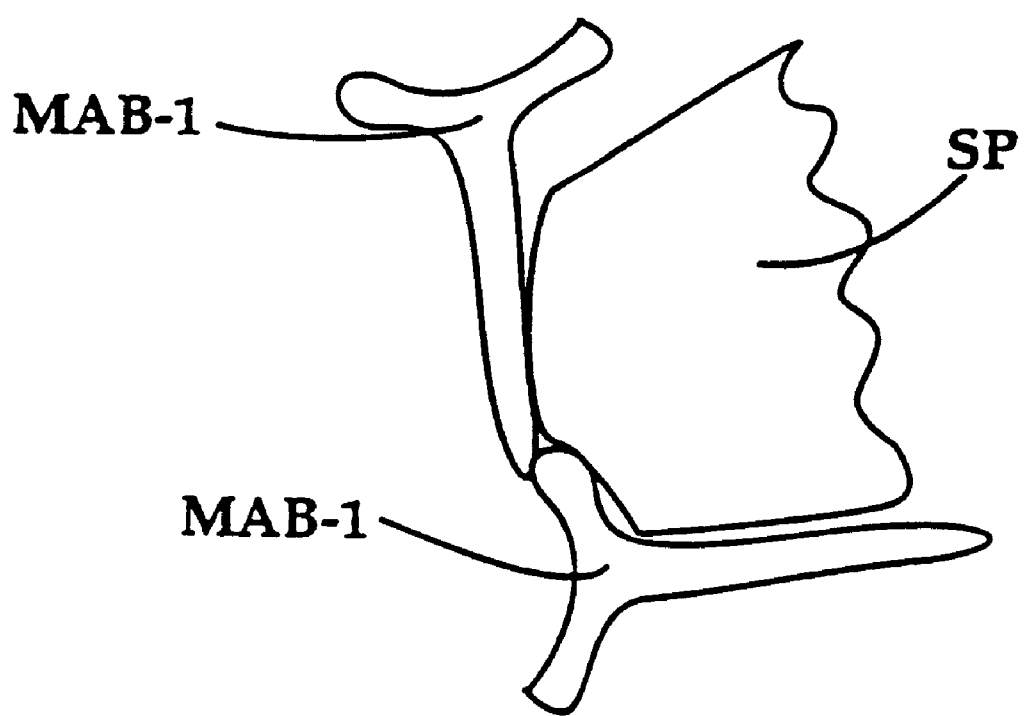
FIG. 5 shows a labeled monoclonal antibody which consists of several antibody molecules attached to a labeling staining particle in a pad of the device of FIG. 3.

The first antibody region 22 contains labeled MAb-1, the intact condition of which is schematically shown in FIG. 5. As shown in this figure, labeled MAb-1 consists of several antibody molecules attached to a detectable marker, in this case illustrated as a stained particle, SP.

If a rupture is present, the sample will contain free IGFBP-1. As soon as the sample is introduced into the first antibody region 22 via aperture 50, any free IGFBP-1 present in the sample will specifically bind to labeled MAb-1 by its specific binding site BS 1, as illustrated in FIG. 6.

The complex consisting of SP, MAb-1, and free IGFBP-1 will then migrate through the material of the first antibody region 22 into the nitrocellulose strips 24 and 26 forming filtering regions 25 and 27. This movement occurs simultaneously in both directions, which essentially reduces the test time as compared to known one-pad one-strip devices. However, for ease of the description, the processes which occur in the test device will be considered separately in nitrocellulose strips 24 and 26.

When the SP-MAb-1-free IGFBP-1 complex reaches filtering region 25, the complex continues moving toward test region 28. When the complex reaches test region 28, free IGFBP-1 contained in the complex binds to MAb-2 which is immobilized to the material of the nitrocellulose strip 24 in test region 28. Illustrated in FIG. 7 is the SP-MAb-1-free IGFBP-1-MAb-2 formed. The complex is attached to MAb-2 through its specific binding site BS 2 and is captured against further movement. Within 5 to 10 minutes, the stained particles SP attached to the SP-MAb-1-free IGFBP-1-MAb-2 complex accumulate in a sufficient concentration in test region 28 that they become distinctly visible to a naked eye in the form of a dark line (not shown). This is used as a qualitative indication of the presence of rupture in the fetal membrane.

The amount of free IGFBP-1 that can be detected according to this device is dependent on the minimum concentration of detectable marker that can be detected by the user. Using a fluorescent label, it should be possible to further enhance the detection limits of the device relative to stained particles. However, fluorescent labels require a light source to cause the labels to fluoresce. Thus, an advantage of stained particles and colored dyes is that no additional instrumentation is needed in order to operate the device.

The device according to this embodiment also includes first and second control regions 30 and 32. First control region 30 serves to indicate when the sample has little or no free IGFBP-1. When little or no free IGFBP-1 is present in the sample, some of the labeled MAb-1 originally present in first antibody region 22 does not have free IGFBP-1 to which to bind. As a result, instead of becoming immobilized in test region 28, the labeled MAb-1 migrates past test region 28 into region 36. In such instances, the detectable marker does not accumulate in test region 28. Absent a control region, one would not know whether the absence of detectable marker in the test region 28 was due to an absence of free IGFBP-1 in the sample or device failure.

First control region 30 serves to capture labeled MAb-1 which did not bind to free IGFBP-1 in the sample and can be used to indicate that the sample has little or no free IGFBP-1. Control region 32 has the same composition as test region 28 and serves to indicate that the device is working by showing that the sample has flowed from the first antibody region 22 to control region 32.

The functioning of the first and second control regions 30 and 32 will now be described with regard to two scenarios, i.e, where the sample contains little or no free IGFBP-1 and where the sample contains a large amount of free IGFBP-1.

In the first scenario where the sample does not contain free IGFBP-1, or contains a very small amount of IGFBP-1, e.g., about 10–40 ng/mL (i.e., $10^{-9}$ g to $40^{-9}$ g). Labeled MAb-1, which is free of free IGFBP-1, will migrate toward test region 28 (FIG. 3). Simultaneously labeled MAb-1 will migrate toward the first and second control regions 30 and 32. Labeled MAb-1 is available in this first scenario to migrate toward the first and second control regions 30 and 32.

Figure 8:
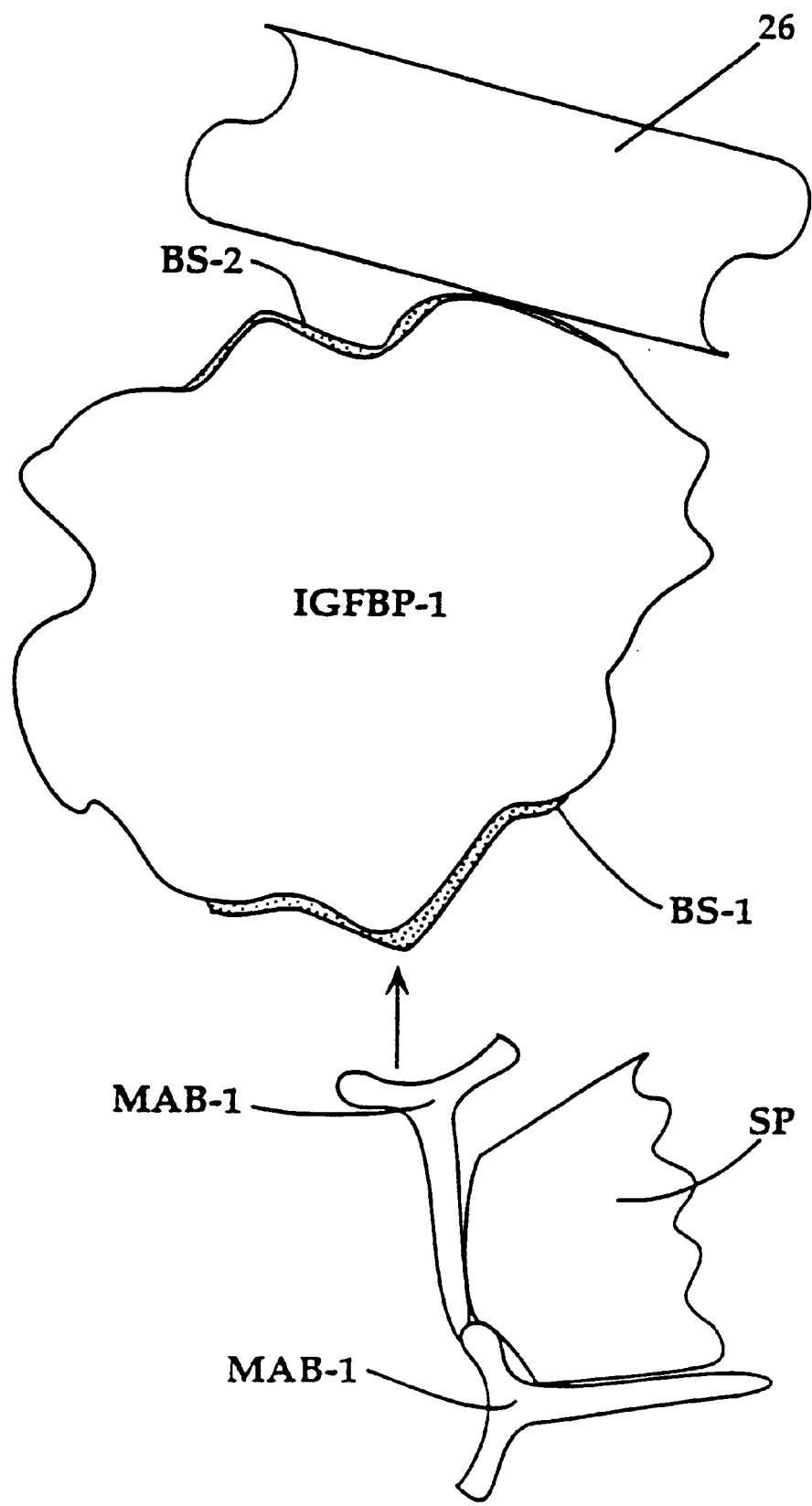
FIG. 8 illustrates the same complex of FIG. 5 in its movement toward free IGFBP-1 fixed to a nitrocellulose strip of a control region.
Figure 9:
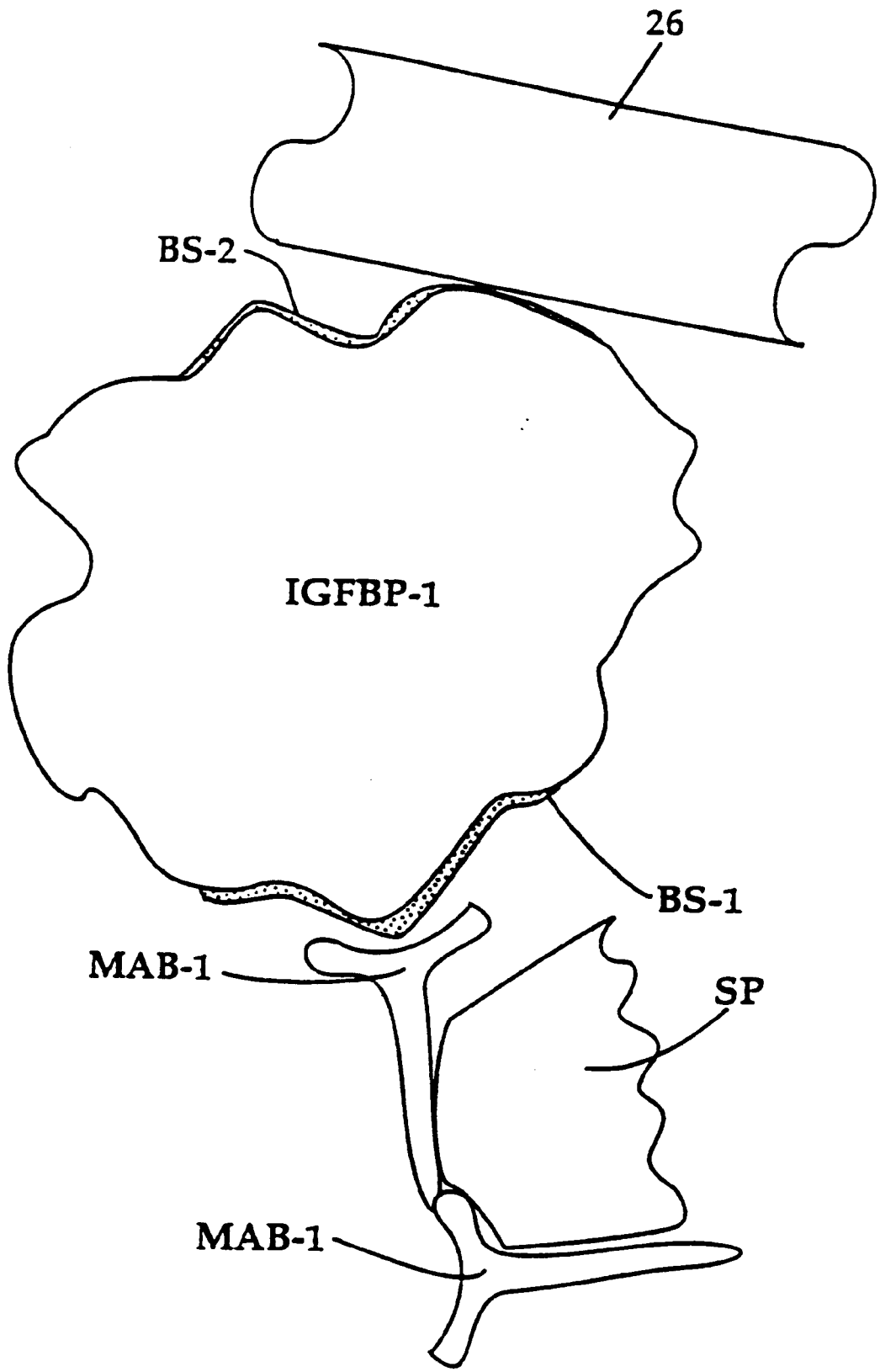
FIG. 9 shows the same complex as in FIG. 8 attached to the respective binding site of free IGFBP-1.

The labeled MAb-1 which migrates to the first control region 30 will attach to binding site BS 1 of the free IGFBP-1 molecule which has been immobilized in the first control region 30 (FIGS. 8 and 9). As this process continues, the accumulated stained particles SP connected to MAb-1 will be visible to a naked eye as a colored line in the first control region 30. The appearance of stained particles SP in the first control region 30 serves to confirm the migration of the sample within the device and can also be used to indicate that only a small amount of free IGFBP-1 is present in the sample.

In the second scenario where free IGFBP-1 is present in the vaginal secretion sample in significant quantities, free IGFBP-1 will bind to labeled MAb-1 in the first antibody region 22 and will migrate toward the first and second control regions 30 and 32. The first control region 30 does not present a barrier to the SP-MAb-1-free IGFBP-1 complex since the first control region 30 is looking to bind to labeled MAb-1 which is not bound to free IGFBP-1. Hence, the SP-MAb-1-free IGFBP-1 complex will migrate past the first control region 30 and reach the second control 32 where it will bind to MAb-2 which is bound therein. The second control region 32 is identical to the test region 28 and hence will immobilize the SP-MAb-1-free IGFBP-1 complex. As a result, the second control region 32, will be colored and visible, thus proving that the test device is operative and is suitable for use.

The test device of the above type (i.e., a one-pad-two-strip system) makes it possible to detect free IGFBP-1 over a wide range of concentrations of free IGFBP-1 in the sample without affecting the function of the control region. This is achieved, in particular, due to the fact that the complex of free IGFBP-1 with labeled MAb-1 does not pass through the test region. This is important feature, because in the case of a high concentration of free IGFBP-1, their accumulation in the test region of the one-strip system will sharply decrease the staining ability of the positive control region containing free IGFBP with labeled MAb-1.

As far as low concentrations are concerned, the device of the invention is very sensitive, even to minute concentrations of free IGFBP-1 (about 5 ng/mL) in the sample. The detection limit of test device can be further reduced by using detectable labels, such as fluorescent marker, which can be observed at even lower concentrations.

The device also includes a first control region 30 which can be used to positively detect the presence of a low concentration of free IGFBP-1 in the sample. As discussed above, the first control region 30 will be strongly colored when the concentration of free IGFBP-1 in the sample is low. This is because, in the latter case, a significant amount of labeled MAb-1 will remain free, i.e., not captured by free IGFBP-1 contained in the sample.

Although the method and device have been shown and described in the form of specific embodiments, these embodiments, their parts, materials, and configurations have been given only as examples, and that other modifications of the system are possible. For example, the ELISA test used for quantitative determination of free IGFBP-1 can be replaced by other methods known in the field of immunochemistry, such radioimmunoassay. The staining particles may be other than those listed. The test device was illustrated in the form of a strip, although it may have any other configuration. Strips 24 and 26 were described as being made of nitrocellulose. However, it should be understood that other porous materials may be used including, for example, fiberglass fabric, porous plastic and filter paper. The pad forming the first antibody region 22 can be made of other materials than glass fiber fabric, such as porous plastic. The device was described with reference to specific dimensions. It is understood that these dimensions are given as an example and do not limit the scope of the invention. Although the entire method and device relate to free IGFBP-1, the principle of the method and the structure of the device can be employed for qualitative determination of the presence of any other protein, including a carrier protein, in any medium, and in a very wide range of concentrations.

6. Accuracy of the Device for Detecting Fetal Membrane Ruptures

The accuracy of a device according to the present invention for detecting fetal membrane ruptures was evaluated by comparing the results obtained by using the device to the results obtained by using a quantitative ELISA-based assay.

In this study, a group of 71 pregnant women were tested. Each woman was examined and assessed by two different methods to determine whether or not a fetal membrane rupture had occurred. In one approach, a qualitative procedure was performed using the device described in Example 5 and illustrated in FIGS. 3–9 to detect the occurrence of a fetal membrane rupture. In an alternative approach, a quantitative ELISA-based analysis was employed.

The accuracy of the fetal membrane rupture diagnosis provided by the device was evaluated in terms of (1) sensitivity, (2) predictive value, and (3) specificity. For this study, "sensitivity" was defined as the ratio between the number of patients with a true positive test result and the number of patients with either a true positive test result or a false negative test result;

"predictive value" was defined as the ratio between the number of patients with a true positive test result and the number of patients with either a true positive test result or a false positive test result;

"specificity" was defined as the ratio between the number of patients with a true negative test result and the number of patients with either a true negative test result or a false positive test result;

a "true positive test result" was defined as one in which the device-based analysis indicated that a fetal membrane rupture had occurred and the results of the quantitative ELISA-based analysis indicated that a fetal membrane rupture had occurred;

a "false positive test result" was defined as one in which the device-based analysis indicated that a fetal membrane rupture had occurred and the results of the quantitative ELISA-based analysis indicated that a fetal membrane rupture had not occurred;

a "true negative test result" was defined as one in which the device-based analysis indicated that a fetal membrane rupture had not occurred and the results of the quantitative ELISA-based analysis indicated that a fetal membrane rupture had not occurred; and a "false negative test result" was defined as one in which the device-based analysis indicated that a fetal membrane rupture had not occurred and the results of the quantitative ELISA-based analysis indicated that a fetal membrane rupture had occurred.

Howell, et al., *British J. Obstet. and Gynecol.*, 1985, 5, 1141–1144. In this study, it was determined that the device-based method has a sensitivity of 95%, a predictive value of 97%, and a specificity of 97%.

A. Device-based Assay. The test strip device of Example 5 was utilized to detect the occurrence of fetal membrane rupture in each of the test subjects.

The analysis was carried as follows. A few drops (50–200 mL) of a vaginal secretion sample were pipetted on the sample application pad. After 5–10 minutes, the device was inspected by the naked eye. The results were considered to be positive if (i) the test region 28 was stained, and (ii) either both or one of the control regions was also stained. The results were considered to be negative if at least one of the control regions was stained. The device was determined to be non-functioning if neither test region 28 or control regions 30 or 32 were stained.

It was assumed that weak staining of test region 28 corresponded to concentrations of free IGFBP-1 from about 5 to 15 ng/mL.

The results of the test conducted on the entire group of patients are summarized in Table 7.

B. Quantitative Method: ELISA Assay An ELISA-based test was used to determine the concentration of free-IGFBP in vaginal secretion samples.

50 microliters of a diluted (⅕) vaginal secretion sample were introduced into wells of a 96 well Linbro plate (Linbro Co.). Each well was sensitized by addition of a solution of the second monoclonal antibody (MAb-2, 10 μg/mL) dissolved in PBS.

To plot a calibration curve, a solution of free IGFBP-1 was added to eight of the sensitized wells in the following respective amounts (ng/mL) 100, 50, 25, 12, 6, 3, 1.5, 0.7. The plate was incubated at room temperature for 1 hour, with shaking.

After intensive washing, a solution of MAb-1/horseradish peroxidase conjugate (50 microliter (1 μg/mL) was added to each well, followed by a 15 minute incubation at room temperature in a shaker.

The wells were then washed out, and a solution of ortho-phenylenediamine with $H_2O_2$ was added to each well. The plate was then incubated for 10 minutes. The reaction was stopped by addition of 1N $H_2SO_4$. Absorbance was measured in each of the wells at a wavelength of 492 nm, as described above.

A calibration curve was plotted using the abscissa axis for optical density units and ordinate axis for concentration of free IGFBP-1. The generated calibration curve was used to quantitatively determine the concentration of free IGFBP-1 in each of the vaginal secretion samples contained in the remaining wells of the same plate.

TABLE 7

DETECTION OF THE FREE IGFBP-1 IN VAGINAL SECRETION SAMPLES IN PATIENTS WITH CLINICALLY VERIFIED DIAGNOSIS OF FETAL MEMBRANE RUPTURE

| Patient No. | Free IGFBP-1 Strip Test (+/−) | IGFBP-1 (ng/mL) ELISA Test | Clinical Diagnosis of Rupture (yes, no, suspicion) |
|---|---|---|---|
| 1 | − | 0 | no |
| 2 | + | 30 | yes |
| 3 | + | 250 | yes |
| 4 | + | 10 | yes |
| 5 | + | >500 | yes |
| 6 | − | 0 | no |
| 7 | − | 0 | no |
| 8 | − | 0 | no |
| 9 | − | 0 | no |
| 10 | − | 0 | no |
| 11 | + | 120 | yes |
| 12 | + | 20 | yes |
| 13 | + | 1000 | yes |
| 14 | + | 1000 | yes |
| 15 | + | 18 | no |
| 16 | − | 0 | no |
| 17 | − | 0 | no |
| 18 | − | 0 | no |
| 19 | − | 0 | no |
| 20 | − | 0 | no |
| 21 | − | 0 | no |
| 22 | + | 240 | yes |
| 23 | + | 100 | yes |
| 24 | − | 0 | no |
| 25 | − | 7.5 | yes |
| 26 | − | 0 | no |
| 27 | + | 100 | yes |
| 28 | + | 200 | yes |
| 29 | + | 80 | yes |
| 30 | + | 14 | yes |
| 31 | − | 0 | no |
| 32 | − | 0 | no |
| 33 | − | 0 | no |
| 34 | − | 0 | no |
| 35 | − | 0 | no |
| 36 | + | 3.5 | suspicion |
| 37 | + | 2.5 | yes |
| 38 | + | 500 | yes |

TABLE 7-continued

DETECTION OF THE FREE IGFBP-1 IN VAGINAL SECRETION SAMPLES IN PATIENTS WITH CLINICALLY VERIFIED DIAGNOSIS OF FETAL MEMBRANE RUPTURE

| Patient No. | Free IGFBP-1 Strip Test (+/−) | IGFBP-1 (ng/mL) ELISA Test | Clinical Diagnosis of Rupture (yes, no, suspicion) |
|---|---|---|---|
| 39 | + | 9 | yes |
| 40 | − | 0 | no |
| 41 | − | 0 | no |
| 42 | − | 0 | no |
| 43 | − | 0 | no |
| 44 | + | 3840 | yes |
| 45 | + | 26 | yes |
| 46 | − | 0 | no |
| 47 | + | 12 | yes |
| 48 | − | 0 | no |
| 49 | − | 0 | no |
| 50 | + | 8 | yes |
| 51 | − | 0 | no |
| 52 | + | 1000 | yes |
| 53 | + | 15 | yes |
| 54 | − | 0 | no |
| 55 | − | 0 | no |
| 56 | − | 0 | no |
| 57 | − | 0 | no |
| 58 | − | 12 | yes |
| 59 | + | 5 | suspicion |
| 60 | + | 1000 | yes |
| 61 | − | 0 | no |
| 62 | + | 75 | yes |
| 63 | + | 30 | yes |
| 64 | − | 0 | no |
| 65 | + | 7000 | yes |
| 66 | + | 20000 | yes |
| 67 | + | 22000 | yes |
| 68 | + | 24000 | yes |
| 69 | + | 24000 | yes |
| 70 | + | 16000 | yes |
| 71 | + | 14000 | yes |

C. Analysis of Study Results

The character of a given test result as either a true positive, false positive, true negative or false negative test result was determined by comparing the result obtained from a device-based test for a given patient to the result obtained by the ELISA-based assay. As shown in Table 7, the following results were obtained using the device-based method: 35 true positives, 33 true negatives, 1 false positive, and 2 false negatives. Using the formulas defined above for sensitivity, predictive value, and specificity and the results summarized in Table 7, the device-based test results were found to have a sensitivity of 95%, a predictive value of 97%, and a specificity of 97%.

The sensitivity, predictive value, and specificity of the device-based assay were compared to the sensitivity, predictive value, and specificity achieved using the total IGFBP-1 assay and the ROM-Check Membrane Immunoassay described in Rutanen, E. M., et al., Clin. Chim. Acta, 1993, Vol. 214, pp. 73–81). As can be seen from the results summarized in Table 8, the device-based method was found to be significantly more accurate than the results obtained using the other two methods.

TABLE 8

| Indices | Free IGFBP-1 (pres. inv.) | Total IGFBP-1 (compar. ex)* | Rom-Check Membrane Immunoassay* |
|---|---|---|---|
| Sensitivity | 95 | 75 | 92 |
| Predictive Value | 97 | 97 | 80 |

TABLE 8-continued

| Indices | Free IGFBP-1 (pres. inv.) | Total IGFBP-1 (compar. ex)* | Rom-Check Membrane Immunoassay* |
|---|---|---|---|
| Specificity | 97 | 95 | 79 |
| False Positive Results | 1.4 | 3 | 20 |
| False Negative Results | 2.0 | 25 | 9 |

*Rutanen E.M., et al. Clin. Chim. Acta, 1993, Vol. 214, pp. 73–81).

7. Unidirectional Device with Control Region

A device having two control regions in which the test region and control regions are on the same fluid path is described in this example and illustrated in FIG. 11. In this embodiment, the device includes a strip-like body composed of several sequentially interconnected elements. More specifically, a central part of the device comprises a first antibody region 52 which contains MAb-1 labeled with a detectable marker.

Connected to an end of the first antibody region 52 is a first nitrocellulose strip 54, which is used to form a test region 58 and first and second control regions 60, 62. Located in an intermediate position of nitrocellulose strip 54 is a test region 58 which is arranged transversely to the device over its entire width. Test region 58 is a portion of nitrocellulose material of strip 54 which is impregnated by MAb-2. Test region 58 may be located, e.g., at a distance of 5 mm from the end of the first antibody region 52, and may have a width of 1 mm. Test region 58 operates in an identical manner as the test region 28 described in Example 7.

Located distal to the test region 58 are two transverse control regions, i.e., first control region 60 and second control region 62, which also may cross the entire width of nitrocellulose strip 54. The space between the first and second control regions 60 and 62 may be about 1 mm.

Second control region 62 is identical to test region 58 in that it is impregnated by MAb-2. Meanwhile, the first control region 60 is impregnated with free IGFBP-1. The second control region 62 is positioned distal relative to the first control region 60 such that a sample introduced into the first antibody region 52 migrates past the test region, through the first control region 60 to the second control region 62. The first and second control regions 60 and 62 can operate in a manner identical to the first and second control regions 30 and 32 described in Example 7.

Filter paper strip 64 is connected to the distal end of nitrocellulose strip 54 in order to draw the sample past the test region 58 and control regions 60 and 62.

The device also includes a filter region 55 containing nonlabeled MAb-1 for filtering free IGFBP-1 not bound to the labeled MAb-1. The filtering region 55 containing non-labeled MAb-1 is positioned on a portion of the length of the nitrocellulose strip 54 between first antibody region 52 and test region 58.

An aperture 72 is provided on the front side of the device for the introduction of a sample of vaginal secretions.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method of determining the presence or amount of free insulin-like growth factor binding protein-1 (IGFBP-1) uncomplexed to insulin-growth factor-1 (IGF-1) and insulin-growth factor-2 (IGF-2) in a biological fluid sample, comprising:

reacting said biological fluid sample with (i) a first anti-IGFBP-1 monoclonal antibody which specifically binds to said free IGFBP-1, and (ii) a second anti-IGFBP-1 monoclonal antibody which specifically binds to said free IGFBP-1 to form an immune complex, where each of said first and second monoclonal antibodies do not inhibit the binding of the other to said free IGFBP-1, and where binding of said first and second antibodies to said free IGFBP-1 is inhibited in the presence of said IGF-1 or said IGF-2, and one of said first and second antibodies is produced by a cell line identified by ATCC designation HB-12279 and the other of said first and second antibodies is produced by a cell line identified by ATCC designation HB-12280, and determining the presence or amount of said immune complex formed to determine the presence or amount of said free IGFBP-1 in said biological fluid sample.

2. The method of claim 1 wherein said first antibody is labeled with a detectable label and said determining step comprises measuring the label in said immune complex.

3. The method of claim 2 wherein said label is selected from the group consisting of colloidal gold, an enzyme, a dye, and a radioactive isotope.

4. The method of claim 3, wherein said second monoclonal antibody is affixed to a solid support, and whereby said determining step comprises measuring the label bound to said support in said immune complex.

5. The method of claim 1, wherein said first monoclonal antibody is produced by the cell line identified by ATCC designation HB-12279.

6. The method of claim 1, wherein said first monoclonal antibody is produced by the cell line identified by ATCC designation HB-12280.

* * * * *